United States Patent
Tierney

(10) Patent No.: US 9,074,234 B2
(45) Date of Patent: Jul. 7, 2015

(54) METHOD OF PREDICTING CROP YIELD USING METABOLIC PROFILING

(75) Inventor: Timothy Tierney, Minnetonka, MN (US)

(73) Assignee: Syngenta Participations AG, Basel (CH)

(*) Notice: Subject to any disclaimer, the term of this patent is extended or adjusted under 35 U.S.C. 154(b) by 533 days.

(21) Appl. No.: 13/414,252

(22) Filed: Mar. 7, 2012

(65) Prior Publication Data

US 2013/0139277 A1 May 30, 2013

Related U.S. Application Data

(60) Provisional application No. 61/450,017, filed on Mar. 7, 2011.

(51) Int. Cl.
*G01N 33/50* (2006.01)
*G01N 33/48* (2006.01)
*G06G 7/75* (2006.01)
*C12Q 1/02* (2006.01)

(52) U.S. Cl.
CPC .............. *C12Q 1/02* (2013.01); *G01N 33/5038* (2013.01); *G06G 7/75* (2013.01); *G01N 33/48* (2013.01); *G01N 33/5097* (2013.01)

(58) Field of Classification Search
CPC .......... G01N 33/5038; G01N 33/5097; G01N 33/48; G06G 7/75
USPC .................. 800/260, 266, 267; 702/19; 703/2
See application file for complete search history.

(56) References Cited

U.S. PATENT DOCUMENTS

| 2006/0064772 A1 | 3/2006 | Kriz et al. |
| 2007/0231864 A1 | 10/2007 | Havkin-Frenkel et al. |
| 2009/0070898 A1 | 3/2009 | Allen et al. |
| 2009/0193543 A1 | 7/2009 | Sanz Molinero |
| 2010/0145625 A1* | 6/2010 | Altmann et al. ............... 702/19 |
| 2014/0189903 A1 | 7/2014 | Duncan et al. |

OTHER PUBLICATIONS

Seebauer et al., "Amino Acid Metabolism in Maize Earshoots. Implications for Assimilate Preconditioning and Nitrogen Signaling," Plant Physiology, Dec. 2004, vol. 136, pp. 4326-4334.*
Zhang et al., "Review: Nutrient Loading of Developing Seeds," Functional Plant Biology, 2007, 34, 314-331.*
Howarth et al., Co-ordinated Expression of Amino Acid Metabolism in Response to N and S Deficiency During Wheat Grain Filling., Journal of Experimental Botany, vol. 59, No. 13, pp. 3675-3689, 2008.*
Basso et al., "Review of Crop Yield Forecasting Methods and Early Warning Systems", http://www.fao.org/fileadmin/templates/ess/documents/meetings_and_workshops/GS_SAC_2013/Improving_methods_for_crops_estimates/Crop_Yield_Forecasting_Methods_and_Early_Warning_Systems_Lit_review.pdf, 2013.*
Steinfath et al., Discovering Plant Metabolic Biomarkers for Phenotype Prediction Using an Untargeted Approach, Plant Biotechnology Journal (2010) 8, pp. 900-911.*

* cited by examiner

*Primary Examiner* — Anne Grunberg
(74) *Attorney, Agent, or Firm* — Karen Moon Bruce

(57) ABSTRACT

The present invention relates to agricultural business methods that may be used in conjunction with a novel technology that can predict the yield of a given plant.

16 Claims, 1 Drawing Sheet

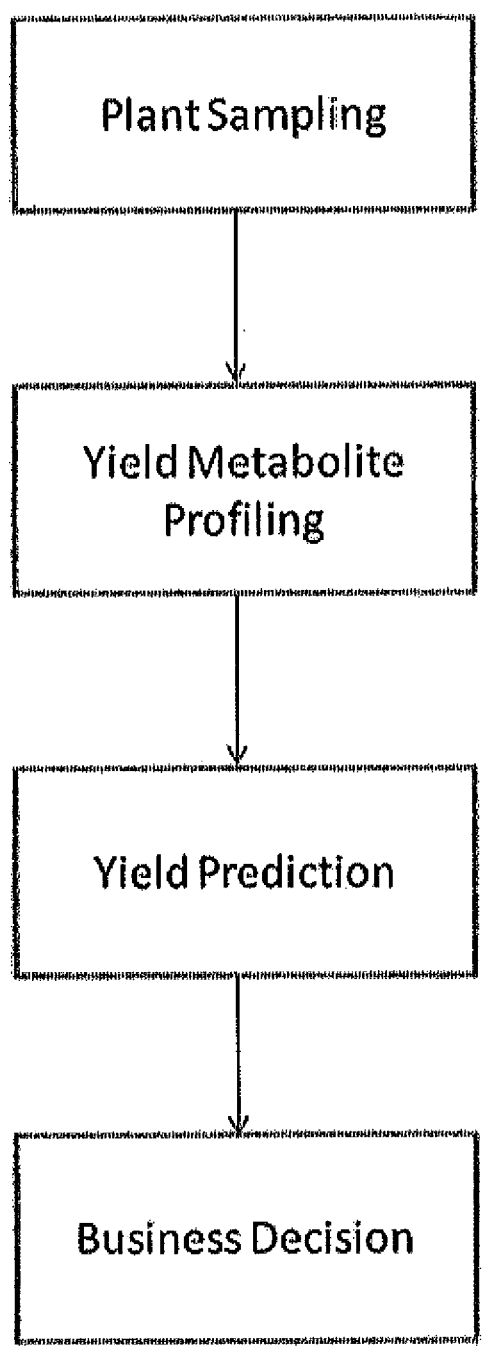

```
                        SEQUENCE LISTING

<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Phe, Tyr, Trp or Leu
<220> FEATURE:
<221> NAME/KEY: MISC_FEATURE
<222> LOCATION: (6)..(11)
<223> OTHER INFORMATION: Xaa is any naturally occurring amino acid
<220> FEATURE:
<221> NAME/KEY: MISC_FEATURE
<222> LOCATION: (12)..(12)
<223> OTHER INFORMATION: Xaa is Asp, Glu, Asn, Gln, Ser, Thr, Ala or Lys
<220> FEATURE:
<221> NAME/KEY: MISC_FEATURE
<222> LOCATION: (13)..(13)
<223> OTHER INFORMATION: Xaa is Ser or Ala
<220> FEATURE:
<221> NAME/KEY: MISC_FEATURE
<222> LOCATION: (14)..(14)
<223> OTHER INFORMATION: Xaa is Asp or Glu
<220> FEATURE:
<221> NAME/KEY: MISC_FEATURE
<222> LOCATION: (15)..(16)
<223> OTHER INFORMATION: Xaa is any naturally occurring amino acid
<220> FEATURE:
<221> NAME/KEY: MISC_FEATURE
<222> LOCATION: (17)..(17)
<223> OTHER INFORMATION: Xaa is Leu, Ile, Val, Met, Phe or Tyr

<400> SEQUENCE: 1

Xaa Asp Gly Ser Ser Xaa Xaa Xaa Xaa Xaa Xaa Xaa Xaa Xaa Xaa Xaa
1               5                   10                  15

Xaa

<210> SEQ ID NO 2
<211> LENGTH: 18
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Phe, Tyr, Trp or Leu
<220> FEATURE:
<221> NAME/KEY: MISC_FEATURE
<222> LOCATION: (6)..(12)
<223> OTHER INFORMATION: Xaa is any naturally occurring amino acid
<220> FEATURE:
<221> NAME/KEY: MISC_FEATURE
<222> LOCATION: (13)..(13)
<223> OTHER INFORMATION: Xaa is Asp, Glu, Asn, Gln, Ser, Thr, Ala or Lys
<220> FEATURE:
<221> NAME/KEY: MISC_FEATURE
<222> LOCATION: (14)..(14)
<223> OTHER INFORMATION: Xaa is Ser or Ala
<220> FEATURE:
<221> NAME/KEY: MISC_FEATURE
<222> LOCATION: (15)..(15)
<223> OTHER INFORMATION: Xaa is Asp or Glu
```

```
<220> FEATURE:
<221> NAME/KEY: MISC_FEATURE
<222> LOCATION: (16)..(17)
<223> OTHER INFORMATION: Xaa is any naturally occurring amino acid
<220> FEATURE:
<221> NAME/KEY: MISC_FEATURE
<222> LOCATION: (18)..(18)
<223> OTHER INFORMATION: Xaa is Leu, Ile, Val, Met, Phe or Tyr

<400> SEQUENCE: 2

Xaa Asp Gly Ser Ser Xaa Xaa Xaa Xaa Xaa Xaa Xaa Xaa Xaa Xaa
1               5                   10                  15

Xaa Xaa

<210> SEQ ID NO 3
<211> LENGTH: 19
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Phe, Tyr, Trp or Leu
<220> FEATURE:
<221> NAME/KEY: MISC_FEATURE
<222> LOCATION: (6)..(13)
<223> OTHER INFORMATION: Xaa is any naturally occurring amino acid
<220> FEATURE:
<221> NAME/KEY: MISC_FEATURE
<222> LOCATION: (14)..(14)
<223> OTHER INFORMATION: Xaa is Asp, Glu, Asn, Gln, Ser, Thr, Ala or Lys
<220> FEATURE:
<221> NAME/KEY: MISC_FEATURE
<222> LOCATION: (15)..(15)
<223> OTHER INFORMATION: Xaa is Ser or Ala
<220> FEATURE:
<221> NAME/KEY: MISC_FEATURE
<222> LOCATION: (16)..(16)
<223> OTHER INFORMATION: Xaa is Asp or Glu
<220> FEATURE:
<221> NAME/KEY: MISC_FEATURE
<222> LOCATION: (17)..(18)
<223> OTHER INFORMATION: Xaa is any naturally occurring amino acid
<220> FEATURE:
<221> NAME/KEY: MISC_FEATURE
<222> LOCATION: (19)..(19)
<223> OTHER INFORMATION: Xaa is Leu, Ile, Val, Met, Phe or Tyr

<400> SEQUENCE: 3

Xaa Asp Gly Ser Ser Xaa Xaa Xaa Xaa Xaa Xaa Xaa Xaa Xaa Xaa
1               5                   10                  15

Xaa Xaa Xaa

<210> SEQ ID NO 4
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is any naturally occurring amino acid
<220> FEATURE:
```

```
<221> NAME/KEY: MISC_FEATURE
<222> LOCATION: (4)..(5)
<223> OTHER INFORMATION: Xaa is any naturally occurring amino acid

<400> SEQUENCE: 4

Gly Xaa Gly Xaa Xaa Gly
1               5
```

METHOD OF PREDICTING CROP YIELD USING METABOLIC PROFILING

STATEMENT REGARDING ELECTRONIC SUBMISSION OF A SEQUENCE LISTING

A Sequence Listing in ASCII text format, submitted under 37 C.F.R. §1.821, entitled 73101_US_REG_ORG_NAT_1_21 May 2013_SeqListing_ST25.txt, 4 KB in size, generated on May 21, 2013 and filed via EFS-Web is provided in lieu of a paper copy. This Sequence Listing is hereby incorporated by reference into the specification for its disclosure.

FIELD OF THE INVENTION

The present invention relates to agricultural methods that may be used in conjunction with a technology that can predict the yield of a given plant all disclosed herein.

BACKGROUND OF THE INVENTION

Plant yield is a very complex trait involving on a molecular basis the interaction of many pathways and interacting factors. There has been a tremendous amount of focus in the field of commercial agriculture over the past decade to develop higher yielding plants either through traditional plant breeding or genetic modifications. In a simplified view, the yield of a plant ultimately depends on the energy the plant gains through fixing carbon dioxide into carbohydrates during photosynthesis. The primary plant tissue involved in photosynthesis are the leaves and to a lesser extent the stem tissue. All other tissues such as the roots and seed are dependent on the photoassimilates made in the photosynthetic tissue. In general, this can be seen as an energy flow from photsynthetically active tissues to photosynthetically inactive tissues.

Phloem transport of this energy is determined by the relative locations of the areas of supply and utilization of the products of photosynthesis. Translocation occurs from areas of supply (sources) to areas of metabolism of storage (sinks). Sources include any exporting organ, typically a mature leaf that is capable of producing photosynthate in excess of its own needs. The direction of phloem transport of this energy is determined by the relative locations of the areas of supply and utilization of the products of photosynthesis. Another type of source is a storage organ during the exporting phase of its development. For example, a storage root may be a sink during the first growing season when it accumulates sugars received from the source leaves. During the second growing season the same root could become a source, when the stored sugars are remobilized and utilized to produce a new shoot which ultimately becomes reproductive. Sinks include any non-photosynthetic organs of the plant and organs that do not produce enough photosynthetic products to support their own growth or storage needs. Roots, tubers, developing fruits and immature leaves which must import carbohydrate for normal development are all examples of sink tissues. Sink tissues differ in their ability to attract source products. Elements such as stress, developmental stages of plant tissues, and osmotic potential all may affect the transport of photoassimilates.

Differential distribution of photoassimilates within the plant is termed partitioning. Partitioning of assimilated carbon amongst sink organs is a critical factor that controls rate and pattern of plant growth. The regulation of the diversion of fixed carbon into the various metabolic pathways is termed allocation. The rate of fixed carbon in a source cell can be classified into three principle categories; storage, utilization, and transport. Starch is synthesized and stored within chloroplasts and in most species is a primary storage form that is mobilized for translocation during the night. Fixed carbon can be utilized within various compartments of the photosynthesizing cell to meet energy needs of the cell or provide carbon skeletons for the synthesis of other compounds required by the cells. Fixed carbon can also be incorporated into transport sugars for export to various sink tissues.

The rate of photosynthesis of leaves is strongly influenced by the demands of the sink. There are cases in which senescent leaves can be rejuvenated to full photosynthetic performance when the sink/source ratio is increased substantially. On the other hand rapid growth of a sink can sometimes compete with leaves for remobilizable nitrogen leading to senescence of the leaf and a drop in its photosynthetic capacity. Young leaves normally act as a sink rather than as a source. After a certain time however they begin to export carbohydrates to the phloem although import carbohydrate may continue for a while through different vascular strands. Once sucrose begins to actively load into companion cells and then into the sieve elements, water will enter by osmosis and flow will begin out of the line of veins. The leaf will become a source instead of a sink.

Two primary photoassimilates are sugar and starch, and these products are important to yield and plant development. Sugar and starch biochemistry are interrelated in plants. (See, e.g., Sivak, M. N. and J. Preiss (1994). Starch synthesis in seeds. In: Seed development and germination. Kigel, J. and G. Galili, eds. (Marcel Dekker, New York), pp. 139-168; J. S. Hawker (1985). Sucrose. In: Biochemistry of storage carbohydrates in green plants. P. M. Dey and R. A. Dixon, Eds., (Academic Press, London), pp. 1-51, which are incorporated herein by reference).

During the early development of storage organs, such as seeds and tubers, sucrose is imported and used for building the cellular components required for growth and development. Following this phase the metabolic program changes to convert the imported sucrose into storage compounds such as starch in tubers and fatty acids in oil seeds. Metabolism is finally altered to convert the starch and oils into reduced carbon compounds for the development of sprouts and seedlings respectively. Sucrose levels rise when hexoses decrease apparently terminating cell division in initiating differentiation and storage activities.

Early ear development in species belonging to the grass family Poaceae (e.g. wheat, maize, wheat, etc) relies upon concurrent photosynthate transport into reproductive sink tissue, as the developing seed cannot utilize stored photoassimilates present in other plant tissues. Because the seed are weak sinks, it is unable to attract stored reserves from source tissues. Seed abortion may occur when concurrent photosynthate is insufficient to meet the needs of reproductive growth, resulting in dramatically decreased yield, or in the case of maize ear, barreness. Anthesis is generally recognized as the critical period of ear and kernel development. Varied experimental approaches have demonstrated that treatments, which decrease the plant carbon exchange rate (CER) around anthesis, decrease grain yield. For example, large yield losses occur when maize plants are shaded (Early et al., 1967; Schussler and Westgate, 1991; Andrade et al., 1993), defoliated (Tollenaar and Daynard, 1978), subjected to water-deficits (Denmead and Shaw, 1960; Claassen and Shaw, 1970; Moss and Downey, 1971; Westgate and Boyer, 1986; Schussler and Westgate, 1991) or exposed to high plant density (Prine, 1971; Baenziger and Glover, 1980) around anthesis. Conversely, treatments that increase plant CER around anthesis increase grain yield. For example, yield enhancements are obtained when maize plants are provided supplemental radiation (Schoper et al., 1982; Ottman and Welch, 1988). In all cases, the variation in yield was directly related to the number of kernels that developed and supply of concurrent photosynthate. Collectively, these results suggest that kernel number may be limited by carbohydrate supply, particularly during drought stress at anthesis.

One aspect that has not been looked at in detail, is whether or not metabolic profiling in these source and/or sink tissues may give insight into the more subtle processes such as sugar and stress signaling. Metabolic profiling has become a powerful tool in the discovery of processes, interactions, compounds and pathways that might be involved in various biological phenomena. According to the invention, further exploration into metabolite profiling of reproductive sink tissue has led to some unexpected findings that certain metabolite profiles can be utilized to make a determination as to predicting yield of an individual plant. Accordingly, data from single plants can be further statistically validated to predict the yield of a given plant population. The ability to correlate yield with the presence or absence of specific metabolites and/or combinations thereof in reproductive sink tissue have many useful applications that will be described further herein.

SUMMARY OF THE INVENTION

The methods herein provide novel methods of predicting a plant's yield through the measurement of specific metabolites either individually or in combination with one another in a specific plant reproductive sink tissue and business methods that can be employed to better mitigate risks associated with commercial agriculture. The plant predictive methods described herein may be used to predict yield of plant populations as well as allow for more efficient crop management practices (e.g. amount and timing of chemical applications or amount of irrigation water applied to a field). Further embodiments employ these predictive methods to better calculate crop insurance rates based upon risk associated with growing and harvesting a given crop.

Further provided are methods of utilizing the yield predictive methods described herein to develop fast (transgenic and/or native trait) plant evaluation methods to select for high yielding lines, calculate insurance rates, provide better crop forecasting capabilities and means to better prepare for grain handling and transportation.

These and other features, objects and advantages of the present invention will become better understood from the description that follows. The description of preferred embodiments is not intended to limit the invention to cover all modifications, equivalents and alternatives. Reference should therefore be made to the embodiments recited herein for interpreting the scope of the invention.

BRIEF DESCRIPTION OF DRAWINGS

FIG. 1 demonstrates a typical workflow using the novel yield predicting methods.

DEFINITIONS

The practice of the present invention will employ, unless otherwise indicated, conventional techniques of botany, microbiology, tissue culture, molecular biology, chemistry, biochemistry, plant quantitative genetics, statistics and recombinant DNA technology, which are within the skill of the art. Such techniques are explained fully in the literature. See, e.g., Langenheim and Thimann, (1982) Botany: Plant Biology and Its Relation to Human Affairs, John Wiley; Cell Culture and Somatic Cell Genetics of Plants, vol. 1, Vasil, ed. (1984); Stanier, et al., (1986) The Microbial World, 5th ed., Prentice-Hall; Dhringra and Sinclair, (1985) Basic Plant Pathology Methods, CRC Press; Maniatis, et al., (1982) Molecular Cloning: A Laboratory Manual; DNA Cloning, vols. I and II, Glover, ed. (1985); Oligonucleotide Synthesis, Gait, ed. (1984); Nucleic Acid Hybridization, Hames and Higgins, eds. (1984); and the series Methods in Enzymology, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention.

As used herein the singular forms "a", "and", and "the" include plural reference unless the context clearly dictates otherwise. Thus, for example, reference to "a vector" is a reference to one or more vectors and includes equivalents thereof known to those skilled in the art.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent.

As used herein, the word "or" means any one member of a particular list and also includes any combination of members on that list.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the embodied composition, method or structure.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), O-Beta Replicase systems, transcription-based amplification system (TAS) and strand displacement amplification (SDA). See, e.g., Diagnostic Molecular Microbiology: Principles and Applications, Persing, et al., eds., American Society for Microbiology, Washington, D.C. (1993). The product of amplification is termed an amplicon.

A "control plant" or "control" as used herein may be a non-transgenic plant of the parental line used to generate a transgenic plant herein. A control plant may in some cases be a transgenic plant line that includes an empty vector or marker gene, but does not contain the recombinant polynucleotide of the present invention that is expressed in the transgenic plant being evaluated. A control plant in other cases is a transgenic plant expressing the gene with a constitutive promoter. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "NUE nucleic acid" means a nucleic acid comprising a polynucleotide ("NUE polynucleotide") encoding a full length or partial length NUE polypeptide.

As used herein "operably linked" includes reference to a functional linkage between a first sequence, such as a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

A preferred embodiment of the invention is use of the methods disclosed herein to predict a given phenotype (i.e. yield) for plants belonging to the plant family Poaceae. The Poaceae plant family comprises, as known in the art, many agronomically important grasses such as for example corn, wheat, rice, and sorghum.

Herein the term "growing season" or "growth cycle" interchangeably refers to a time period when a plant is undergoing active growth. As used herein, the phrase "one growing season" refers to the period from planting of a plant seed to the maturation of a plant and finally to the point where a plant is no longer undergoing active growth. The plant may cease active growth through natural processes (i.e. reaching the end of a growth cycle) or by other means such as harvest.

As used herein, "yield" may include reference to bushels per acre of a grain crop at harvest, as adjusted for grain moisture (15% typically for maize, for example), and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated. Yield can be affected by many properties including without limitation, plant height, pod number, pod position on the plant, number of internodes, incidence of pod shatter, grain size, efficiency of nodulation and nitrogen fixation, efficiency of nutrient assimilation, carbon assimilation, plant architecture, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Yield of a plant of the can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are common practice in the art.

"Derived from" is used to mean taken, obtained, received, traced, replicated or descended from a source (chemical and/or biological). A derivative may be produced by chemical or biological manipulation (including, but not limited to, substitution, addition, insertion, deletion, extraction, isolation, mutation and replication) of the original source.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

"Overexpression" refers to the level of expression in transgenic organisms that exceeds levels of expression in normal or untransformed organisms.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The term "transformation" refers to the transfer of a nucleic acid fragment into the genome of a host cell, resulting in genetically stable inheritance. "Transiently transformed" refers to cells in which transgenes and foreign DNA have been introduced (for example, by such methods as *Agrobacterium*-mediated transformation or biolistic bombardment), but not selected for stable maintenance. "Stably transformed" refers to cells that have been selected and regenerated on a selection media following transformation.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term "translational enhancer sequence" refers to that DNA sequence portion of a gene between the promoter and coding sequence that is transcribed into RNA and is present in the fully processed mRNA upstream (5') of the translation start codon. The translational enhancer sequence may affect processing of the primary transcript to mRNA, mRNA stability or translation efficiency. "Visible marker" refers to a gene whose expression does not confer an advantage to a transformed cell but can be made detectable or visible. Examples of visible markers include but are not limited to Beta-glucuronidase (GUS), luciferase (LUC) and green fluorescent protein (GFP).

"Wild-type" refers to the normal gene, virus, or organism found in nature without any known mutation.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

The phrase "abiotic stress" as used herein refers to any adverse effect on metabolism, growth, reproduction and/or viability of a plant by abiotic factors (i.e. water availability, heat, cold, and etc). Accordingly, abiotic stress can be induced by suboptimal environmental growth conditions such as, for example, salinity, water deprivation, water deficit, drought, flooding, freezing, low or high temperature (e.g., chilling or excessive heat), toxic chemical pollution, heavy metal toxicity, anaerobiosis, nutrient deficiency, nutrient excess, atmospheric pollution or UV irradiation.

The phrase "abiotic stress tolerance" as used herein refers to the ability of a plant to endure an abiotic stress without suffering a substantial alteration in metabolism, growth, productivity and/or viability.

As used herein "water deficit" means a period when water available to a plant is not replenished at the rate at which it is consumed by the plant. A long period of water deficit is colloquially called drought. Lack of rain or irrigation may not produce immediate water stress if there is an available reservoir of ground water for the growth rate of plants. Plants grown in soil with ample groundwater can survive days without rain or irrigation without adverse affects on yield. Plants grown in dry soil are likely to suffer adverse affects with minimal periods of water deficit. Severe water deficit stress can cause wilt and plant death; moderate drought can cause reduced yield, stunted growth or retarded development. Plants can recover from some periods of water deficit stress without significantly affecting yield. However, water deficit stress at the time of pollination can have an irreversible effect in lowering yield. Thus, a useful period in the life cycle of corn, for example, for observing water deficit stress tolerance is the late vegetative stage of growth before tasseling. Water deficit stress tolerance is determined by comparison to control plants. For instance, plants of this invention can survive water deficit stress with a higher yield than control plants. In the laboratory and in field trials drought can be simulated by giving plants of this invention and control plants less water than is given to sufficiently-watered control plants and measuring differences in traits. One aspect of the invention provides plants overexpressing the genes as disclosed herein which confers a higher tolerance to a water deficit.

As used herein, the phrase "water optimization" refers to any measure of a plant, its parts, or its structure that can be measured and/or quantified in order to assess an extent of or a rate of plant growth and development under different conditions of water availability. As such, a "water optimization trait" is any trait that can be shown to influence yield in a plant under different sets of growth conditions related to water availability. Exemplary measures of water optimization are grain yield at standard moisture percentage (YGSMN), grain moisture at harvest (GMSTP), grain weight per plot (GWTPN), and percent yield recovery (PYREC).

As used herein, the phrases "drought tolerance" and "drought tolerant" refer to a plant's ability to endure and/or thrive under conditions where water availability is suboptimal. In general, a plant is labeled as "drought tolerant" if it displays "enhanced drought tolerance." As used herein, the phrase "enhanced drought tolerance" refers to a measurable improvement, enhancement, or increase in one or more water optimization phenotypes as compared to one or more control plants.

Water Use Efficiency (WUE) is a parameter frequently used to estimate the tradeoff between water consumption and $CO_2$ uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of $CO_2$ uptake to water vapor loss from a leaf or portion of a leaf, often measured over a very short time period (e.g. seconds/minutes) (Kramer, 1983, p. 406). The ratio of $13 C/12 C$ fixed in plant tissue, and measured with an isotope ratio mass-spectrometer, also has been used to estimate WUE in plants using $C_3$ photosynthesis (Martin et al., 1999, Crop Sci. 1775). As used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients. It is contemplated that the transgenic plants produced by the methods described herein will confer an increase in water use efficiency.

The phrase "biotic stress" as used herein refers to any adverse effect on metabolism, growth, reproduction and/or viability of a plant by biotic factors (i.e. insect pressure, disease and etc).

The phrase "biotic stress tolerance" as used herein refers to the ability of a plant to endure an biotic stress without suffering a substantial alteration in metabolism, growth, reproduction and/or viability.

As used herein the phrase "plant biomass" refers to the amount (measured in grams of air-dry or dry tissue) of a tissue produced from the plant in a growing season, which could also determine or affect the plant yield or the yield per growing area.

As used herein the phrase "plant vigor" refers to the amount (measured by weight) of tissue produced by the plant in a given time. Hence increased vigor could determine or affect the plant yield or the yield per growing time or growing area.

The term "early vigor" refers to active healthy well-balanced growth especially during early stages of plant growth, and may result from increased plant fitness due to, for example, the plants being better adapted to their environment (optimizing the use of energy resources and partitioning between shoot and root). Plants having early vigor also show increased seedling survival and a better establishment of the crop, which often results in highly uniform fields (e.g. crops growing in a uniform fashion, such as the crops reaching various stages of development at substantially the same time), and often higher yields. Therefore, early vigor may be determined by measuring various factors, such as thousand kernel weight, percentage germination, percentage emergence, seedling growth, seedling height, root length, root and shoot biomass and many more.

As used herein, "seedling vigor" refers to the plant characteristic whereby the plant emerges from soil faster, has an increased germination rate (i.e., germinates faster), has faster and larger seedling growth and/or germinates faster under cold conditions as compared to the wild type or control under similar conditions. Seedling vigor has often been defined to comprise the seed properties that determine "the potential for rapid, uniform emergence and development of normal seedlings under a wide range of field conditions".

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase where the floral organs are produced. If the appropriate environmental and developmental signals the plant switches to floral, or reproductive, growth are disrupted, the plant will not be able to enter reproductive growth, therefore maintaining vegetative growth.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

As used herein, the term "allele" refers to any of one or more alternative forms of a gene, all of which relate to at least one trait or characteristic. In a diploid cell, two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates to SNPs, it is in some instances more accurate to refer to a "haplotype" (i.e., an allele of a chromosomal segment) instead of "allele". However, in such instances, the term "allele" should be understood to comprise the term "haplotype".

As used herein, the phrase "associated with" refers to a recognizable and/or assayable relationship between two entities. For example, a trait, locus, QTL, SNP, gene, marker, phenotype, etc. is "associated with resistance" if the presence or absence of the trait, locus, QTL, SNP, gene, marker, phenotype, etc., influences an extent or degree of tolerance.

As used herein, the term "backcross", and grammatical variants thereof, refers to a process in which a breeder crosses a progeny individual back to one of its parents, for example, a first generation hybrid F1 with one of the parental genotypes of the F1 hybrid. In some embodiments, a backcross is performed repeatedly, with a progeny individual of one backcross being itself backcrossed to the same parental genotype.

The term "chromosome" is used herein in its art-recognized meaning of the self-replicating genetic structure in the cellular nucleus containing the cellular DNA and bearing in its nucleotide sequence a linear array of genes.

As used herein, the terms "cultivar", "line" and "variety" refer to a group of similar plants that by structural or genetic features and/or performance can be distinguished from other varieties within the same species.

As used herein, the term "gene" refers to a hereditary unit including a sequence of DNA that occupies a specific location on a chromosome and that contains the genetic instruction for a particular characteristics or trait in an organism.

As used herein, the term "heterozygous" refers to a genetic condition existing when different alleles reside at corresponding loci on homologous chromosomes.

As used herein, the term "homozygous" refers to a genetic condition existing when identical alleles reside at corresponding loci on homologous chromosomes.

As used herein, the term "hybrid" in the context of nucleic acids refers to a double-stranded nucleic acid molecule, or duplex, formed by hydrogen bonding between complementary nucleotide bases. The terms "hybridize" or "anneal" refer to the process by which single strands of nucleic acid sequences form double-helical segments through hydrogen bonding between complementary bases.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous individual or line.

As used herein, the phrase "informative fragment" refers to a nucleic acid molecule and/or its nucleotide sequence that allows for the proper identification of which allele of an allele pair (e.g., an SNP) the nucleic acid molecule and/or the nucleotide sequence corresponds to.

As used herein, the terms "introgression", "introgressed", and "introgressing" refer to both a natural and artificial process whereby genomic regions of one species, variety, or cultivar are moved into the genome of another species, variety, or cultivar, by crossing those species. The process can optionally be completed by backcrossing to the recurrent parent.

As used herein, the term "linkage" refers to a phenomenon wherein alleles on the same chromosome tend to be transmitted together more often than expected by chance if their transmission was independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

In some embodiments, "linkage" implies physical proximity on a chromosome. Thus, two loci are linked if they are within 50 centiMorgans (cM) of each other. As such, two loci are linked if they are in some embodiments less than 10, in some embodiments 9, in some embodiments 8, in some embodiments 7, in some embodiments 6, in some embodiments 5, in some embodiments 4, in some embodiments 3, in some embodiments 2, and in some embodiments 1 centiMorgans (cM) of each other. For example, an SNP is linked to a marker if it is in some embodiments within 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "locus" refers to a position that a given gene or a regulatory sequence occupies on a chromosome of a given species. Thus, a "locus" is a chromosomal region where a polymorphic nucleic acid, trait determinant, gene or marker is located. For example, a "gene locus" is a specific chromosome location in the genome of a species where a specific gene can be found.

As used herein, the term "marker" refers to an identifiable position on a chromosome the inheritance of which can be monitored. In some embodiments, a marker comprises a known or detectable nucleic acid sequence.

A "metabolite marker" refers to any metabolite (e.g. glutamine, glucoside of glutamate, 5-oxoproline, aspartate, arginine, proline, phosphate, homoserine-lactone, leucine, putrescine, asparagine and the like) which can be measured in a plant part and correlated to a plant phenotype and/or trait.

One aspect of the invention is the correlation of metabolite marker(s) to a plant's yield potential. Herein, "yield potential" or "future yield potential" interchangeably refers to the yield a plant will produce at a future time point following pollination (e.g. at harvest or seed at seed). A preferred embodiment of the invention measures for metabolite marker(s) in a specific plant tissue prior to pollination such as un-pollinated female inflorescence tissue. The presence and/or absence of these metabolite markers can then be used to predict the approximate yield of a given plant post-pollination (e.g. at seed maturity, or harvest).

As used herein, the phrase "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion and deletion mutations (INDEL), microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, the term "offspring" plant refers to any plant resulting as progeny from a vegetative or sexual reproduction from one or more parent plants or descendants thereof. For instance an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings of F1s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the term "phenotype" refers to a detectable characteristic of a cell or organism, which characteristics are at least partially a manifestation of gene expression.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like. Herein the term "un-pollinated female inflorescence tissue" refers to any un-pollinated female reproductive tissue of a plant (e.g. spiklet, bracht, spikelet meristem, inflorescence stalk tissue, and immature floral tissue). The term also refers to all associated and/or adjacent tissues that attach to said un-pollinated female inflorescence tissue.

As used herein, the term "population" refers to a genetically heterogeneous collection of plants sharing a common genetic derivation.

As used herein, the term "primer" refers to an oligonucleotide which is capable of annealing to a nucleic acid target allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH).

As used herein, the term "regenerate", and grammatical variants thereof, refers to the production of a plant from tissue culture.

As used herein, the term "tolerant" and "tolerance" encompass both partial and full tolerance to herbicide injury (e.g., phytotoxicity caused by a HPPD inhibiting herbicide). For HPPD inhibiting herbicides, "phytotoxicity" occurs in a range from minor chlorosis (discoloration) to necrosis. A susceptible plant can either be non-tolerant or have lower levels of tolerance to herbicide damage relative to a tolerant plant. The term is used to include such separately identifiable forms of resistance as "full resistance", "immunity", "intermediate resistance", "partial resistance", and "hypersensitivity".

The term "crop" encompasses any type of edible or inedible agricultural product, grain, oilseed, fiber, fruit, nut, seed or vegetable or any other material produced by a genetically modified plant or non-genetically modified plant.

DETAILED DESCRIPTION OF THE INVENTION

The embodiments herein provide methods and compositions related to predicting plant yield utilizing an unexpected correlation of specific plant metabolite levels in sampled un-pollinated plant reproductive tissue and employment of this technology to various agricultural business practices (i.e. better management of harvesting, crop insurance risk management, etc). In a preferred embodiment the sampled un-pollinated plant reproductive tissue is un-pollinated female inflorescence tissue. In some embodiments the tissue may be sampled from the stalk of the un-pollinated inflorescence tissue. The business methods herein, make use of this predictive method to better manage various aspects relative to commercial agriculture such as crop insurance, crop forecasting, management of future transportation needs and costs, planning for harvesting of crop materials and application of chemistry, fertilizer and/or irrigation water.

Plant metabolites taken from un-pollinated plant reproductive tissue and/or adjacent tissue that may be correlated with predicted plant yield, herein referred to as "yield metabolite markers" may include but are not limited to amino acids, nutrients (e.g. phosphate, calcium, nitrogen, etc), organic acids, organic bases, sugars (simple or complex), proteins, nucleic acids or molecules containing fatty acid chains. In preferred embodiments the yield metabolite markers comprise either individually or any combination of glutamine, 5-oxoproline, aspartate, arginine, proline, phosphate, homoserine-lactone, leucine and asparagine. In one embodiment the yield metabolite markers comprise either individually or any combination of glutamine, glucoside of glutamate, 5-oxoproline, aspartate, arginine, proline, phosphate, homoserine-lactone, leucine, asparagines, putrescine, valine, vanillate, threonine, adenine, aminpentanoate, erythritol, nicotinate ribonucleoside, arginine, 1,3-dihydroxyacetone, isoleucylglutamate, lysine, methyl-2-oxopentanoate, 3-methoxytyrosine, N6-acetyllysine, 2-aminoadipate, and the like. In one embodiment, the yield metabolite markers are selected from one or more of glutamine, glucoside of glutamate, 5-oxoproline, aspartate, arginine, proline, phosphate, homoserine-lactone, leucine, asparagines, and putrescine. In another embodiment, the yield metabolite markers comprise glutamine, valine and vanillate. In another embodiment, the yield metabolite markers include homoserine lactone, threonine, adenine, aminpentanoate, erythritol, nicotinate ribonucleoside, arginine, 1,3-dihydroxyacetone, isoleucylglutamate, lysine, and methyl-2-oxopentanoate. In another embodiment, the yield metabolite markers include markers that are positively correlated with yield, such as, but not limited to, glutamine, glucoside of glutamate, 5-oxoproline, aspartate, arginine, proline, phosphate, homoserine-lactone, leucine, asparagines, and putrescine. Alternatively, the yield metabolite markers could include one or more markers that are negatively correlated with yield, such as, but not limited to, 3-methoxytyrosine, N6-acetyllysine and 2-aminoadipate. In another embodiment, the yield metabolite marker is glutamine.

The embodiments disclosed herein may be used to predict yield in any monocot or dicot plant for example but not limited to maize, soybean, barley, alfalfa, sunflower, canola, soybean, cotton, peanut, sorghum, tobacco, sugar beet, rice, wheat, rye, turfgrass, millet, sugarcane, tomato, or potato and can be employed into various agricultural business methods relative to these crops. In a preferred embodiment the invention may be used to predict yield in a monocot plant or plant population. A further preferred embodiment is the invention may be used to predict yield (i.e. grain yield) in a plant selected from the Poaceae or "true grass" family (e.g. maize, rice, wheat and sorghum). The methods described herein may also be employed in predicting yield in either transgenic or non-transgenic plants.

Some aspects of the invention may relate to the prediction of grain yield in a plant wherein the grain yield may be predicted in a unit per plant. For example one may be enabled by the teachings described herein to predict the amount of biomass weight per plant or grain weight per plant. In some embodiments one may calculate the approximate number of kernels produced per plant. In some aspects one may be able to predict the amount of a plant product that may be produced from a plant and or plant population for instance, the amount of ethanol predicted to be produced from a relative plant yield prediction.

It is contemplated in that one may use common statistical methods to sample a subset of plants from a homogenous population of plants and use the methods described herein to predict the approximate combined yield of said homogenous population of plants. This method would be highly valuable in commercial agriculture in that one could for example predict the amount of grain a given crop population will yield. Using these predictions, a grower could anticipate whether or not more fertilizer should be applied to the field. In some instances, one could use these methods to anticipate irrigation water usage and future transportation requirements/costs for the storage and movement of seed.

In one aspect of the invention, the yield metabolite markers are measured in any one of or in combination with spikelet tissue, bract tissue spikelet meristem tissue, inflorescence stalk tissue or immature floral tissue from a monocot plant. In a preferred embodiment the monocot plant is a member of the Poaceae family. In another aspect of the invention immature ear shoots of maize are sampled for yield metabolite markers whose levels can then be correlated to the plant's predicted yield.

Metabolite profiling was performed to identify small molecules that may be useful in predicting yield in plants. In some aspects these metabolites are measured in specific tissues (e.g. unpollinated female reproductive tissue) or may be measured in any tissue or multiple plant tissues. There are various methods for measuring metabolites including, for example, HPLC (high-performance liquid chromatography), spectrophotometry, enzymatic determination or chemical analysis. Techniques for metabolite profiling are well known in the art. See e.g., U.S. Pat. Nos. 7,005,255; 7,329,489; 7,433,787; 7,550,258; 7,550,260; and 7,553,616 and U.S. Published Application Nos. 20020009740; 20040146853; 20050014132; 20060134676, 20060134677; 20060134678; 20070172820; 20070172885; 20010178599; 20070026389; 20070032969; 20070288174; 20070298998; 20080124752; 20080161228; 20090017464; 20090075284; 20090093971; and 20090155826 all incorporated by reference. Biomarkers of yield identified herein include molecules associated with for example nitrogen use, stress responses, or sugar pathways.

The use of metabolite profiling data allows for the identification of nucleic acids useful in possibly increasing yield in plants which include nucleic acids encoding components of the nitrogen assimilation pathway in plants. In one aspect it may be beneficial to express an protein involved in the nitrogen assimilation pathway specifically in the un-pollinated female reproductive tissue of a plant. Previously described nucleic acids and proteins have not taught how to use such molecules for enhancing drought tolerance in plants.

Specifically, when performing methods as described herein, nucleic acids useful in the invention include (a) full length or functional fragments encoding glutamine synthetase, glutamate dehydrogenase, aspartate aminotransferase, and asparagine synthetase, which may be overexpressed in a plant to thereby confer drought tolerance to the plant and/or for identification of activators of such enzymes; (b) full length or functional fragments encoding allantoinase, allantoate amidohydrolase, and ureidoglycolate amidohydrolase, which may be used for identification of inhibitors of such enzymes; and (c) inhibitory nucleic acids having homology to a nucleic acid encoding allantoinase, allantoate amidohydrolase, and ureidoglycolate amidohydrolase, which may be expressed in a plant to thereby confer drought tolerance to the plant.

The following enzymes and associated referenced accession number and sequences may find use in many in various embodiments as described herein:

Glutamine synthetase (GS, EC 6.3.1.2) catalyzes the ATP-dependent synthesis of glutamine via the condensation of ammonium and glutamate to yield glutamine, which then provides nitrogen groups, either directly or via glutamate, for the biosynthesis of all nitrogenous compounds in the plant. Higher plants have two types of GS isoenzymes that are localized in the cytosol or in the plastid/chloroplasts. Representative nucleic acids encoding cytosolic GS isoenzymes include maize GS1-1, GS1-2, GS1-3, GS1-4, and GS1-5 (GenBank Accession Nos. X65926, X65927, X65928, X65929, and NM_001111827 respectively). A representative nucleic acid encoding a plastid GS isoenzyme is maize GS-2 (GenBank Accession No. X65931). A representative nucleic acid encoding a cytosolic GS isoenzyme from pea (GenBank Accession No. PEAGSCY1A).

Glutamate dehydrogenase (GDH, EC 1.4.1.3) catalyzes the synthesis of glutamate via the condensation of ammonium and alpha ketoglutarate. A representative nucleic acid encoding glutamate dehydrogenase is maize glutamate dehydrogenase (GenBank Accession Nos. gdh1:NM_001111831.1).

Aspartate aminotransferase (AspAT, EC 2.6.1.1) catalyzes the conversion of oxaloacetate to aspartate. A representative nucleic acid encoding aspartate aminotransferase is maize aspartate aminotransferase (GenBank Accession Nos. NM_001155533.1).

Asparagine synthetase (EC 6.3.5.4) catalyzes three distinct chemical reactions: glutamine hydrolysis to yield ammonia takes place in the N-terminal domain. The C-terminal active site mediates both the synthesis of a beta-aspartyl-AMP intermediate and its subsequent reaction with ammonia. The ammonia released is channeled to the other active site to yield asparagine. Representative nucleic acids encoding asparagine synthetase include maize asparagine synthetase 1, asparagine synthetase 2, and asparagine synthetase 3 (GenBank NM_001111997, NP_001131013, AsnS2:NM_001137541, NP_001131014, AsnS3:NM_001137542, NP_001131015, and AsnS4:NM_001137543), respectively. Representative nucleic acids encoding asparagine synthetase 1 from *Glycine max* (GenBank Accession No. U77679.1).

Allantoinase (EC 3.5.2.5) catalyzes the conversion of allantoin to allantoate. Representative nucleic acids encoding allantoinase include maize allantoinase (GenBank Accession No. NM_001148584, EU973141, NP_001142056)respectively. Rice allantoinase (GenBank Accession No. NM_001060821). *Arabidopsis thaliana* allantoinase (GenBank Accession No. NP_567276). A *Robinia pseudocacia* allantoinase nucleic acid (GenBank Accession No. AY466437). A *Saccharomyces cerevisiae* allantoinase nucleic acid (GenBank Accession No. YSCDAL1A).

Allantoate Amidohydrolase (EC 3.5.3.9, allantoate deiminase) catalyzes the conversion of allantoate to ureidoglycine. Representative nucleic acids encoding allantoate amidohydrolase include maize allantoate amidohydrolase (GenBank Accession No. NM_001157773), soybean allantoate amidohydrolase (GenBank Accession No. FJ796239), and *Arabidopsis thaliana* allantoate amidohydrolase (GenBank Accession Nos. NM_118126 and NP_193740.1), respectively.

Ureidoglycolate Amidohydrolase (EC 3.5.3.19) catalyzes the conversion of ureidoglycolate to glycoxylate. Representative nucleic acids encoding ureidoglycolate amidohydrolase include *Arabidopsis thaliana* ureidoglycolate amidohydrolase (GenBank Accession No. NM_123726.3 and NC_003076) and Baker's yeast ureidoglycolate amidohydrolase (GenBank Accession No. UAH: NP_012298, respectively).

Nucleic acid variants of the above-identified sequences, which are useful in the methods of the present invention, are described herein below.

Nucleic acids are deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms nucleic acid molecule or nucleic acid may also be used in place of gene, cDNA, mRNA, or cRNA. Nucleic acids may be synthesized, or may be derived from any biological source, including any organism.

Substantially identical nucleic acids are also identified as nucleic acids that hybridize specifically to or hybridize substantially to the full length of any one of sequences disclosed herein under stringent conditions. In the context of nucleic acid hybridization, two nucleic acid sequences being compared may be designated a probe and a target. A probe is a reference nucleic acid molecule, and a target is a test nucleic acid molecule, often found within a heterogeneous population of nucleic acid molecules. A target sequence is synonymous with a test sequence.

A particular nucleotide sequence employed for hybridization studies or assays includes probe sequences that are complementary to at least an about 14 to 40 nucleotide sequence of a nucleic acid molecule of the present invention. For example, probes may comprise 14 to 20 nucleotides, or even longer where desired, such as 30, 40, 50, 60, 100, 200, 300, or 500 nucleotides or up to the full length of any one sequence as referenced herein. Such fragments may be readily prepared, for example by chemical synthesis of the fragment, by application of nucleic acid amplification technology, or by introducing selected sequences into vectors for recombinant production.

Specific hybridization refers to the binding, duplexing, or hybridizing of a molecule only to a particular nucleotide sequence under stringent conditions when that sequence is present in a complex nucleic acid mixture (e.g., total cellular DNA or RNA). Specific hybridization may accommodate mismatches between the probe and the target sequence depending on the stringency of the hybridization conditions.

Stringent hybridization conditions and stringent hybridization wash conditions in the context of nucleic acid hybridization experiments such as Southern and Northern blot analysis are both sequence-dependent and environment-dependent. Longer sequences hybridize specifically at higher temperatures. An extensive guide to the hybridization of nucleic acids is found in Tijssen, *Laboratory Techniques in Biochemistry and Molecular Biology-Hybridization with Nucleic Acid Probes*, 1993, part I chapter 2, Elsevier, New York, N.Y. Generally, highly stringent hybridization and wash conditions are selected to be about 5° C. lower than the thermal melting point (Tm) for the specific sequence at a defined ionic strength and pH. Typically, under stringent conditions a probe will hybridize specifically to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds., *Molecular Cloning: A Laboratory Manual*, 1989, Cold Spring Harbor Laboratory Press, Cold Spring Harbor, N.Y., for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1M Na+ ion, typically about 0.01 to 1M Na+ ion concentration (or other salts) at pH 7.0-8.3, and the temperature is typically at least about 30° C. Stringent conditions may also be achieved with the addition of destabilizing agents such as formamide. In general, a signal to noise ratio of 2-fold (or higher) than that observed for an unrelated probe in the particular hybridization assay indicates detection of specific hybridization.

The following are examples of hybridization and wash conditions that may be used to identify nucleotide sequences that are substantially identical to reference nucleotide sequences of the present invention: a probe nucleotide sequence hybridizes to a target nucleotide sequence in 7% sodium dodecyl sulphate (SDS), 0.5M NaPO$_4$, 1 mM EDTA at 50° C. followed by washing in 2×SSC, 0.1% SDS at 50° C.; such as, a probe and target sequence hybridize in 7% sodium dodecyl sulphate (SDS), 0.5M NaPO$_4$, 1 mM EDTA at 50° C. followed by washing in 1×SSC, 0.1% SDS at 50° C.; such as, a probe and target sequence hybridize in 7% sodium dodecyl sulphate (SDS), 0.5M NaPO4, 1 mM EDTA at 50° C. followed by washing in 0.5×SSC, 0.1% SDS at 50° C.; such as, a probe and target sequence hybridize in 7% sodium dodecyl sulphate (SDS), 0.5M NaPO4, 1 mM EDTA at 50° C. followed by washing in 0.1×SSC, 0.1% SDS at 50° C.; such as, a probe and target sequence hybridize in 7% sodium dodecyl sulphate (SDS), 0.5M NaPO4, 1 mM EDTA at 50° C. followed by washing in 0.1×SSC, 0.1% SDS at 65° C.; or such as, a probe and target sequence hybridize in a solution of 6×SSC (0.5% SDS) at 65° C. followed by washing in 2×SSC (0.1% SDS) and 1×SSC (0.1% SDS).

A further indication that two nucleic acid sequences are substantially identical is that proteins encoded by the nucleic acids are identical or substantially identical, share an overall three-dimensional structure, or are biologically functional equivalents, as described further herein below. Nucleic acid molecules that do not hybridize to each other under stringent conditions are still substantially identical if the corresponding proteins are substantially identical. This may occur, for example, when two nucleotide sequences encoding a same protein sequence differ as permitted by the genetic code, i.e., nucleotide sequences having degenerate codon substitutions wherein the third position of one or more selected (or all) codons is substituted with mixed-base and/or deoxyinosine residues. See Batzer et al., *Nucleic Acids Res.*, 1991, 19:5081; Ohtsuka et al., *J. Biol. Chem.*, 1985, 260:2605-2608; and Rossolini et al. *Mol. Cell. Probes*, 1994, 8:91-98.

Nucleic acids useful in the invention also can comprise a mutagenized nucleotide sequence, including sequences comprising silent mutations. A mutation may comprise one or more residue changes, a deletion of one or more residues, or an insertion of one or more additional residues.

For example, nucleic acids useful in the invention also comprise nucleic acids of any one of the sequences referenced herein, which have been altered for expression in the host organism to account for differences in codon usage. For example, the specific codon usage in plants differs from the specific codon usage in certain microorganisms. Comparison of the usage of codons within a cloned microbial open reading frame to usage in plant genes (and in particular genes from the target plant) will enable an identification of the codons within the open reading frame that should specifically be changed. Typically plant evolution has tended towards a strong preference of the nucleotides C and G in the third base position of monocotyledons, whereas dicotyledons often use the nucleotides A or T at this position. Plant genes typically have a GC content of more than 35%. Open reading frame sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites. By modifying a gene to incorporate specific codon usage for a particular target transgenic species, problems associated with GC/AT content and illegitimate splicing will be overcome.

Nucleic acids useful in the invention also include nucleic acids complementary to any sequence referenced herein or variants thereof as described herein. Complementary sequences are two nucleotide sequences that comprise antiparallel nucleotide sequences capable of pairing with one another upon formation of hydrogen bonds between base pairs. As used herein, the term complementary sequences means nucleotide sequences which are substantially complementary, as may be assessed by the same nucleotide comparison methods set forth below, or is defined as being capable of hybridizing to the nucleic acid segment in question under relatively stringent conditions such as those described herein. A particular example of a complementary nucleic acid segment is an antisense oligonucleotide.

When preparing any of the foregoing nucleic acid variants encoding a functional glutamine synthetase, glutamate dehydrogenase, aspartate aminotransferase, or asparagine synthetase enzyme, it is expected that conservative amino acid changes introduced in identifiable functional domains of such enzymes would not result in a change of enzymatic activity. Such identifiable functional domains are summarized below with respect to representative sequences. By performing routine alignments between the disclosed representative sequences and variant sequences described herein, one skilled in the art could readily identify corresponding functional domains in the variant sequences as well. Likewise, it is expected that conservative or non-conservative amino acid substitutions introduced outside of such domains would also not result in a change of enzymatic activity.

A conservatively substituted variant refers to a polypeptide comprising an amino acid sequence in which one or more residues have been conservatively substituted with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Glutamine synthetase possess a beta Grasp domain having the consensus sequence [FYWL]-D-G-S-S-x(6,8)-[DENQSTAK]-[SA]-[DE]-x(2)-[LIVMFY], and ATP binding domain, and a catalytic glutamate-ammonia ligase activity domain. The locations of the beta-Grasp domain and catalytic domains are exemplified by GS1-5, GS1-1, and GS2. For example, GS1-5 has a beta-Grasp domain (this binding site is referred to on PFAM as pfam03951) that includes amino acids 17-97 and a catalytic domain that includes amino acids 103-354 (pfam00120). GS1-1 has a beta-Grasp domain (pfam03951) that includes amino acids 68-148 and a catalytic domain that includes amino acids 154-405. GS2 has a beta-Grasp domain (pfam03951) that includes amino acids 17-97 and a catalytic domain that includes amino acids 103-353. The crystal structure of GS has been described, which can also be used to identify residues that may be changed while preserving the enzyme structure and function. See Unno et al., *J. Biol. Chem.*, 2006, 281(39):29287-29296.

Glutamine synthetase possess a beta Grasp domain having the consensus sequence [FYWL]-D-G-S-S-x(6,8)-[DENQSTAK]-[SA]-[DE]-x(2)-[LIVMFY] (SEQ ID NOS: 1-3), and ATP binding domain, and a catalytic glutamate-ammonia ligase activity domain. The locations of the beta-Grasp domain and catalytic domains are exemplified by GS1-5, GS1-1, and GS2. For example, GS1-5 has a beta-Grasp domain (this binding site is referred to on PFAM as pfam03951) that includes amino acids 17-97 and a catalytic domain that includes amino acids 103-354 (pfam00120). GS1-1 has a beta-Grasp domain (pfam03951) that includes amino acids 68-148 and a catalytic domain that includes amino acids 154-405. GS2 has a beta-Grasp domain (pfam03951) that includes amino acids 17-97 and a catalytic domain that includes amino acids 103-353. The crystal structure of GS has been described, which can also be used to identify residues that may be changed while preserving the enzyme structure and function. See Unno et al., *J. Biol. Chem.*, 2006, 281(39):29287-29296.

Glutamate dehydrogenase contains an ELFV_dehydrogen_N domain that includes amino acids 31-161; a NADP binding domain that includes amino acids 176-402; and a NADP binding site that includes amino acids 215-217, 237-238, 289-290, and 310-312. NAD binding involves numerous hydrogen-bonds and van der Waals contacts, in particular H-bonding of residues in a turn between the first strand and the subsequent helix of the Rossmann-fold topology. Characteristically, this turn exhibits a consensus binding pattern similar to GXGXXG (SEQ ID NO: 4), in which the first 2 glycines participate in NAD(P)-binding, and the third facilitates close packing of the helix to the beta-strand. Glutamate dehydrogenase may contain a second domain in addition to the NADP domain, which is responsible for specifically binding a substrate and catalyzing a particular enzymatic reaction.

Asparagine synthetase 1 from corn has an active site that includes amino acids 2, 50, 75-77, and 98; a dimer interface site that includes amino acids 17, 25, 28, 32-36, 49; a ligand binding site that includes amino acids 231-233, 265-267, 327, 341-343; and a molecular tunnel that includes amino acids 231-233, 265-267, 327, 341-343.

Asparagine synthetase 2 has an active site that includes amino acids 2, 52, 77-79, an 102; a dimer interface site that includes amino acids 20, 28, 31, 34-38, and 51; a ligand binding site that includes amino acids 248-250, 282-284, 344, and 358-360; and a molecular tunnel that includes amino acids 248-250, 282-284, 344, and 358-360.

Asparagine synthetase 3 has an active site that includes amino acids 2, 50, 75-77 and 99; a dimer interface site that includes amino acids 18, 26, 29, 32-36, and 49; a ligand binding site that includes amino acids 232-234, 266-268, 328, 342-344; and a molecular tunnel that includes amino acids 232-234, 266-268, 328, and 342-344.

Asparagine synthetase 4 has an active site that includes amino acids 2, 50, 75-77, and 99; a dimer interface site that includes amino acids 18, 26, 29, 32-36, and 49; a ligand binding site that includes amino acids 232-234, 266-268, 328, and 342-344; and a molecular tunnel that includes amino acids 232-234, 266-268, 328, and 342-344.

Nucleic acids as described herein may be cloned, synthesized, altered, mutagenized, or combinations thereof. Standard recombinant DNA and molecular cloning techniques used to isolate nucleic acids are known in the art. Site-specific mutagenesis to create base pair changes, deletions, or small insertions is also known in the art. See e.g., Sambrook et al. (eds.) *Molecular Cloning: A Laboratory Manual*, 1989, Cold Spring Harbor Laboratory Press, Cold Spring Harbor, N.Y.; Silhavy et al., *Experiments with Gene Fusions*, 1984, Cold Spring Harbor Laboratory Press, Cold Spring Harbor, N.Y.; Glover & Hames, *DNA Cloning: A Practical Approach*, 2nd ed., 1995, IRL Press at Oxford University Press, Oxford/New York; Ausubel (ed.) *Short Protocols in Molecular Biology*, 3rd ed., 1995, Wiley, New York.

The present invention also provides inhibitory nucleic acids having homology to nucleic acids encoding allantoinase, allantoate amidohydrolase, and ureidoglycolate amidohydrolase, which are the targets for inhibition Inhibitory nucleic acids are well-known in the art, including nucleic acids for cosuppression, antisense inhibition, viral-suppression, hairpin suppression, stem-loop suppression, double-stranded RNA-inhibition, and interfering RNAs (e.g., short interfering RNAs (siRNA) and microinterfereing RNAs (miRNA)).

Antisense inhibition refers to the production of antisense RNA transcripts capable of suppressing the expression of the target gene or gene product. Antisense RNA refers to an RNA transcript that is complementary to all or part of a target primary transcript or mRNA and that blocks the expression of a target isolated nucleic acid fragment (U.S. Pat. No. 5,107,065). The complementarities of an antisense RNA may be with any part of the specific gene transcript, i.e., at the 5' non-coding sequence, 3' non-coding sequence, introns, or the coding sequence.

Cosuppression refers to the production of sense RNA transcripts capable of suppressing the expression of the target gene or gene product. Sense RNA is an RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence. See e.g., Vaucheret et al., *Plant J.*, 1998, 16:651-659 and Gura, *Nature*, 2000, 404:804-808.

Another variation describes the use of plant viral sequences to direct the suppression of proximal mRNA encoding sequences. See e.g., PCT International Publication No. WO 98/36083.

Inhibitory nucleic acids may comprise hairpin structures that incorporate all, or part, of an mRNA encoding sequence in a complementary orientation that results in a potential stem-loop structure for the expressed RNA. See e.g., PCT International Publication No. WO 99/53050. In this case, the stem is formed by polynucleotides having homology to the target sequence inserted in either sense or anti-sense orientation with respect to the promoter, and the loop is formed by polynucleotides that do not have a complement in the construct. Hairpin structures may increase the frequency of cosuppression or silencing in the recovered transgenic plants. For a review of hairpin suppression, see Wesley et al., *Methods in Molecular Biology, Plant Functional Genomics: Methods and Protocols*, 2003, 236:273-286 and PCT International Publication Nos. WO 99/61632, WO 02/00894, WO 02/00904.

RNA interference refers to the process of sequence-specific post-transcriptional gene silencing in animals mediated by short interfering RNAs (siRNAs). See e.g., Fire et al., Nature, 1998, 391:806. The corresponding process in plants is commonly referred to as post-transcriptional gene silencing (PTGS) or RNA silencing. The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., *Nature*, 2001, 409:363). Short interfering RNAs derived from dicer activity are typically about 21 to about 23 nucleotides in length and comprise about 19 base pair duplexes (Elbashir et al., *Genes Dev.*, 2001, 15:188). Dicer has also been implicated in the excision of 21- and 22-nucleotide small temporal RNAs (stRNAs) from precursor RNA of conserved structure that are implicated in translational control (Hutvagner et al., *Science*, 2001, 293: 834 (2001)). The RNAi response also features an endonuclease complex, commonly referred to as an RNA-induced silencing complex (RISC), which mediates cleavage of single-stranded RNA having sequence complementarities to the antisense strand of the siRNA duplex. Cleavage of the target RNA takes place in the middle of the region complementary to the antisense strand of the siRNA duplex. In addition, RNA interference can also involve small RNA (e.g., miRNA) mediated gene silencing, presumably through cellular mechanisms that regulate chromatin structure and thereby prevent transcription of target gene sequences. See, e.g., Allshire, *Science*, 2002, 297:1818-1819; Volpe et al., Science, 2002, 297:1833-1837; Jenuwein, Science, 2002, 297:2215-2218; and Hall et al., Science, 2002, 297:2232-2237.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

Sequence complementarities between small RNAs and their RNA targets may determine which mechanism, RNA cleavage or translational inhibition, is employed. While not intending to be limited by a particular mode of action, perfect or near-perfect complementary siRNAs are thought to mediate RNA cleavage, whereas miRNA/target duplexes containing many mismatches may mediate translational inhibition.

MicroRNAs (miRNAs) are noncoding RNAs of about 19 to about 24 nucleotides, which are processed from longer precursor transcripts that range in size from approximately 70 to 200 nt. See e.g., Lagos-Quintana et al., Science, 2001, 294:853-858, Lagos-Quintana et al., Curr. Biol., 2002, 12:735-739; Lau et al., Science, 2001, 294:858-862; Lee et al., Science, 2001, 294:862-864; Llave et al., Plant Cell, 2002, 14:1605-1619 (2002); Mourelatos et al., Genes Dev., 2002, 16:720-728; Park et al., Curr. Biol., 2002, 12:1484-1495; Reinhart et al., Genes Dev., 2002, 16:1616-1626. Processing of miRNA precursors is mediated by DCL1 (previously named CARPEL FACTORY/SHORT INTEGUMENTS1/SUSPENSOR1). See e.g., Park et al., Curr. Biol., 2002, 12:1484-1495; Reinhart et al., Genes Dev., 2002, 16:1616-1626. MicroRNAs (miRNAs) appear to regulate target genes by binding to complementary sequences located in the transcripts produced by these genes. Binding of miRNA may cause downregulation of steady-state levels of the protein encoded by the target mRNA without affecting the transcript itself (see e.g., Olsen and Ambros, Dev. Biol., 1999, 216:671-610) or may cause specific RNA cleavage of the target transcript within the target site (see e.g., Hutvagner et al., Science, 2002, 297:2056-2060; Llave et al., Plant Cell, 2002, 14:1605-1619). Accordingly, it appears that miRNAs can enter at least two pathways of target gene regulation: (1) protein downregulation when target complementarities is <100%; and (2) RNA cleavage when target complementarities is 100%. MicroRNAs entering the RNA cleavage pathway are analogous to the 21-25 nucleotide short interfering RNAs (siRNAs) generated during posttranscriptional gene silencing (PTGS) Inhibitory nucleic acid molecules as described herein above can be used to mediate gene silencing via interaction with RNA transcripts or alternately by interaction with particular gene sequences, wherein such interaction results in gene silencing either at the transcriptional or post-transcriptional level. Inhibitory nucleic acids useful in the invention may have perfect or near-perfect complementarities with a target allantoinase, allantoate amidohydrolase, and ureidoglycolate amidohydrolase molecule, or may have several mismatches.

In general, the process workflow for using yield for making business decision would require plant sampling, followed by yield metabolite profiling, followed by determining yield prediction and finally making a business decision based on the information provided. One aspect of the process, is the use of yield metabolite markers as a method to select for high yielding plant lines. For example, one may measure yield metabolite markers in immature ear shoots of a maize plant and predict yield for a given plant. These high yielding plants could then be used to introgress with hybrid lines and further screened for higher yielding crosses by traditional validation methods of measuring yield from mature plant and/or measuring yield metabolite markers and correlating predicted yield as described herein. The ability to predict yield in a plant also would be a valuable tool in evaluating transgenic and/or non-transgenic traits for yield. Having such a predictive tool would enable one to more quickly evaluate traits for yield as well as reduce costs compared to current practices in that plants would not have to be grown to maturity. Additionally, one may be able to evaluate less plants as to whether or not a given trait would have higher yields relative to controls.

In one aspect of the invention, the methods described herein may be useful in farm management and business methods. For instance, the ability to predict yield in a plant population would enable better crop forecasting abilities than the current methods employed. It is contemplated that sub-sampling of large populations of crops using well known statistical methods and predicting the relative yield of this population would allow for better management of crop harvesting, seed collection and handling and transportation associated with moving harvested materials. For instance, a grower could thus predict how much grain they would obtain from a given population of crops using the methods as described herein. By predicting the amount of grain, a grower can then better plan for and manage such aspects as harvest of the crop, handling and storage of the grain, transportation of the grain and possible income that will be generated from the crop. It is contemplated that the yield prediction methods taught herein may also be highly valuable for organizations such as ethanol plants in that one could predict the amount of ethanol that can be produced from a given population of crops via using the yield prediction methods taught herein for that population of crops. It is also envisioned that the predictive methods disclosed herein, could also be very valuable in predicting associated costs of a given crop such as for example chemical applications, fertilizer or irrigation applications.

Another aspect of the invention is that the methods as described herein may be useful in providing a means to calculate and/or managing risk associated with growing and harvesting crops. For instance, the methods described herein could be useful in evaluating risk(s) of a particular crop. A coefficient reprehensive of this risk then may be used in calculating for example crop insurance rates for a given crop. Farmers use crop insurance to reduce or manage various risks associated with growing crops. Such risks include crop loss or damage caused by weather, hail, drought, frost damage, insects, or disease, for instance. A farmer or grower may desire to grow a crop associated with a particular defined attribute that potentially qualifies for a premium over similar commodity crops, agricultural products, or derivatives thereof. The particular attribute may be associated with the genetic composition of the crop, certain management practices of the grower, or especially in the case of the present invention predicted yield. However, many standard crop insurance policies do not differentiate between commodity crops and crops associated with particular attributes. Accordingly, farmers have a need for crop insurance to cover the risk of growing crops associated with particular attributes. It is contemplated that if a particular crop is expected to result in a high yield as indicated by the methods described herein, one could receive a discounted rate of insurance. For instance the yield predictive methods as described herein could be used in conjunction with any one or more of the business methods as described in U.S. Pat. No. 7,657,469, U.S. Pat. No. 7,039,592, U.S. 20090112637, U.S. 20080086340, U.S. Pat. No. 7,356,406, U.S. 20080040165, U.S. 20060287896, U.S.

20060282294, U.S. 2006001523, U.S. 20060015360, U.S. 20060015374, U.S. 20050125260, U.S. 20050027572, U.S. 20030061075 and U.S. 20020173980 herein all incorporated by reference.

A crop may include any type of edible or inedible agricultural product, grain, oilseed, fiber, fruit, nut, seed, or vegetable or any other material produced by a genetically modified plant or non-genetically modified plant. A defined attribute may comprise one or more of the following characteristics of any crop: organic, organically grown, high oil, high protein, high starch, waxy, highly fermentable, color, grade, classification, weight, nutritionally enhanced, pest resistant, herbicide resistant, pesticide resistant, fungicide resistant, drought tolerant, freeze tolerant, mildew resistant, bacterial resistant, disease resistant, non-genetically modified, genetically modified, genetically altered protein content, genetically altered enzyme content, genetically altered sugar content, genetically altered starch content, high protein, yield enhanced, pharmaceutical traits, precursors or ingredients, pharmaceutical properties, medicinal properties, genetically resistant to cross-pollination (e.g., a teosinte gene cluster introduced into corn deoxyribonucleic (DNA) acid) from neighboring genetically modified crops, and any other crop attributes.

A defined attribute may represent any plant trait associated with a crop, an agricultural product derived from the crop, or both. Further, the defined attribute may comprise a characteristic that is associated with a particular level or range of levels of any of the following: a plant trait, protein, oil, starch in plant material (e.g., harvested grain, fiber or oilseed). For example, soy meal having a certain characteristic (e.g., minimum percent protein content by volume or weight) may be derived from soybeans as the crop. The defined attribute may be, but need not be, defined with respect to a corresponding attribute of a commodity crop, an agricultural product derived from a commodity crop, or another reference.

Although any generally accepted grading standard (e.g., a standard adopted by the Chicago Board of Trade or elsewhere within the marketplace) may be used to define a commodity crop, the generally accepted grading standards may not address a defined attribute or another particular characteristic of interest (e.g., corn with a predicted yield output). Accordingly, the defined attributes may be defined in accordance with one or more of the following items: (1) reference genetic profile (e.g., for pharmaceutical crops or other genetically modified crops), (2) identity of a gene cluster or sequence inserted into plant deoxyribonucleic acid (DNA), (3) a characteristic of a plant resulting from the expression of a genetic trait, or (4) reference growing practices (e.g., for organic crops or specialty crops) or preferentially (5) predicted yield based on the method disclosed herein.

In the U.S., the government (e.g., Federal Grain Inspection Service) establishes grain standards under the United States Grain Standards Act that are suitable for defining commodity grains. The detailed grain standards are currently set forth in 7 C.F.R. §810.101 through §810.2205. Under U.S. grain standards, corn is divided into three classes: yellow, white and mixed; each class may be associated with a grade ranging from U.S. No. 1 to U.S. No. 5. The grades of corn are generally based on minimum test weight per bushel, percentage of heat damage, percentage of broken kernels, and amount of foreign material. Similarly, in the U.S. for commodity soybeans the applicable soybean grades (e.g., U.S. No. 1) are generally based on test weight, heat damage, foreign material content, total damage and splits (e.g., broken seeds).

In another embodiment, the current methods may be used in conjunction with a contractual agreement. For instance, the grower may predict the yield of a crop destined to be used to make for instance a biofuel such as ethanol. In one aspect the grower could use these grain yield predictions to estimate a given amount of ethanol that might be obtained from said crop and base a contractual agreement with an ethanol producer on this information. It may be useful for example, for a grower to guarantee a certain amount of grain to be delivered to a ethanol plant prior to harvest allowing for the ethanol producer and grower to better manage supply of necessary grain to sustain a ethanol plant. Likewise, the methods disclosed herein may be useful in the production of enzymes in plants, cellulosic biofuels, or food/feed distributors.

FIG. 1 demonstrates a typical workflow using the novel yield predicting methods disclosed herein. As shown in the top box labeled "Plant Sampling", one would first sample un-pollinated maternal reproductive tissue(s) (i.e. spikelet tissue, ear shoots, etc). This sampling can be carried out any time prior to pollination and/or harvesting. For instance one may sample at anywhere between 1 to 10 weeks prior to harvesting or in some instances anywhere between 1 to 20 weeks prior to harvesting. When the crop is maize, a preferred embodiment is to sample at the VT-R1 (tasseling to first reproductive stage in maize) phase. In a preferred embodiment of the invention, one will sample multiple subpopulations of a crop population to gain a overall representation of the entire crop population. Population sampling can be accomplished using well known statistical sampling methods known in the art. For example see, *Choosing and Using Statistics: A Biologist Guide* by Calvin Dytham (2011); *Large Sample Methods in Statistics: An Introduction With Applications* by Pranab et. al. (1993) Following plant sampling, the process entails screening the sampled plant tissues for yield metabolites as represented in the box labeled "Yield Metabolite Profiling" of FIG. 1. In some aspects these metabolites are measured in specific tissues (e.g. unpollinated female reproductive tissue) or may be measured in any tissue or multiple plant tissues. Techniques for metabolite profiling are well known in the art. See e.g., U.S. Pat. Nos. 7,005,255; 7,329, 489; 7,433,787; 7,550,258; 7,550,260; and 7,553,616 and U.S. Published Application Nos. 20020009740; 20040146853; 20050014132; 20060134676; 20060134677; 20060134678; 20070172820; 20070172885; 20010178599; 20070026389; 20070032969; 20070288174; 20070298998; 20080124752; 20080161228; 20090017464; 20090075284; 20090093971; and 20090155826 all incorporated by reference. Biomarkers of yield identified herein include molecules associated with for example nitrogen use, stress responses, or sugar pathways. Following yield metabolite profiling, the next step in the workflow as represented by FIG. 1 is "Yield Prediction". Yield prediction can be performed by associating the presence or non-presence of certain yield metabolites such as those disclosed herein with a yield value collected from historical yield data which associates the levels of yield metabolites with yield. For instance, one could a) carry out multiple subsampling of plant tissues from a crop population; b) perform yield metabolite profiling c) harvest the crop population and collect actual yield data; d) compare the yield metabolite data of b) with the actual yield data of c); e) compile a X/Y axis calibration curve to represent the comparison of d). For instance, one could chart the actual yield data on the X-axis and the yield metabolite concentrations on the Y-Axis. f) using the calibration curve of d) one could quickly profile yield metabolites from a plant sample pre-pollination and correlate a predicted yield of said plant or a plant population. It is also understood that one may measure one or more yield metabolites in a tissue and establish certain thresholds that give a predicted range of predicted yields. For example, if a theoretical yield metabolite "A" is measured at <50 ug/ul then the predicted yield would be for example 50-100 bushels per acre. Likewise, one could build upon the threshold for example >50 ug/ul of a relative yield metabolite indicates for instance 100-150 bushels per acre. The following is given just as an example and demonstrates how one could build a fast predictive method for yield. Once the yield is predicted, one may make various business decisions based on the yield prediction which is represented in FIG. 1. For instance, a grower may use the predicted field values of a given crop to plan for seed harvesting, handling, storage and transportation. In another aspect the user may be using predicted yield values to calculate a discount for items such as crop insurance coverage. The predictive methods may also be used in business decisions relative to downstream supply of processes such as biofuel (i.e. ethanol) production, production of enzymes in harvested transgenic plant parts, animal feed or food for human consumption. In another aspect the business decision may be relative to crop forecasting models and in evaluation of overall crop performance in a region which findings could be employed in future plantings (i.e. application of fertilizer, application of various insecticides or herbicides, water usage). In another aspect the business decision might be a means of selecting plant lines for yield in a plant breeding program. It is also contemplated that one may employ yield metabolites (e.g. glutamine measured in un-pollinated reproductive tissue) as yield markers in a plant breeding program. Another aspect is that the business decision may be relative to the evaluation of transgenic plants expressing a suspected gene that confers increased yield for efficacy. For instance, transgenic plants expressing a given gene or genes under evaluation for increased yield could be quickly evaluated using the yield predictive methods described herein. This method could save both money and time in the evaluation of transgenes for increased yield. In another aspect the business decision may assist the grower in entering upon contractual agreements where a certain amount of grain for instance is to be delivered at a future time point. The predictive methods described herein could help said grower to make better estimates of their likely output and allow to better shape the terms of the contract. The above are purely examples of various "business decisions" that could be carried out following the predicting yield of a crop.

EXAMPLES

The following examples have been included to illustrate modes of the invention. Certain aspects of the following examples are described in terms of techniques and procedures found or contemplated by the present co-inventors to work well in the practice of the invention. In light of the present disclosure and the general level of skill in the art, those of skill will appreciate that the following examples are intended to be exemplary only and that numerous changes, modifications, and alterations may be employed without departing from the scope of the invention.

Example 1

Plant Tissue Sampling

Four maize lines (A, B, C, and D) were selected for the study based upon the lack of close genetic relation to each other and because they had shown varied nitrogen use efficiencies in a previous year of testing. The field study was machine planted. A complete factorial in a randomized complete block design with four replications was used in which hybrid and N rate were the treatment factors. Each plot consisted of four rows, 17.5 feet in length and spaced 2.5 feet apart. A soil-applied insecticide (tefluthrin) was applied in furrow at a rate of 0.099 lb a.i. $acre_{-1}$. Weed control consisted of a pre-emergence application of Lumax (S-metolachlor+atrazine+mesotrione) at the labeled rate. N was applied as ammonium sulfate ((NH4)2SO4) in a diffuse band after emergence and incorporated between V2 and V3. The N treatments were applied to between and on either side of the middle two rows of each four row plot. The N rates were 0, 50, 100, 150, and 200 lbs N per acre. The density at harvest was approximately 28,000 plants per acre. Due to destructive sampling of un-pollinated earshoots in one row of each plot, this experiment was harvested by hand (one row per plot). All grain yields are reported in bushels per acre at 15.5% moisture content.

Plants' emerging earshoots at the VT-R1 (tasseling to first reproductive stage in maize) were covered with a shoot-bag and allowed to grow for 5-10 days. After 5-10 days of growth, un-pollinated female inflorescence tissue (earshoot) was collected and flash frozen in liquid nitrogen for further analysis. Three plants were sampled from each plot in four replications with a total of 12 samples from each hybrid. The three plants from each plot were pooled and analyzed as one sample to minimize plant to plant variability. A total of 80 plots (samples) were analyzed. As shown in Table 1 increased application of Nitrogen corresponded to increased yield as expected for each of the four maize lines. Delta Yield was calculated for each of the lines as shown in Table 1. Delta yield is a common comparison of the yield obtained under a nitrogen titration experiment comparing varying rates of nitrogen application. Delta Yield in Table 1 is calculated by subtracting the yield of the 0 N applied treatment (i.e. Treatment 0 lbs. N/ac) from the highest rate of N treatment (i.e. treatment 200 lbs. N/ac). As expected Delta Yield varied from line to line.

TABLE 1

| Nitrogen Rate (lbs. N/ac) | Maize Lines | | | |
| --- | --- | --- | --- | --- |
| | A | B | C | D |
| 0 | 62.8 | 16.4 | 40.8 | 14.6 |
| 50 | 103.1 | 50.6 | 96.8 | 69.1 |
| 100 | 137.9 | 130.1 | 144 | 118.4 |
| 150 | 162.1 | 143 | 161.5 | 123.3 |
| 200 | 190.2 | 165 | 173.1 | 152.6 |
| Delta Yield | 127.4 | 148.6 | 132.3 | 138 |

Example 2

First Metabolic Profiling Study

Samples from Example 1 were ground to a fine powder in a modified shredder under dry ice conditions and then sent for metabolite profiling and statistical analysis. Each sample was then analyzed for 267 metabolites using methods essentially as described in Anal. Chem., 2009, 81 (16), pp 6656-6667; and herein incorporated by reference. For visualization of biochemical differences between the various treatment groups, the data are displayed in line plot format. From this analysis, several metabolites profiled in corn un-pollinated ear shoots were shown to positively correlate with yield. The metabolite glutamine measured from unpollinated ear shoots showed a high correlation to yield (approximately 0.89). Likewise, 5-oxoproline, aspartate, arginine and proline metabolite levels measured in unpollinated ear shoots also correlated to grain yield (>0.80). The table below shows the metabolites with the highest positive correlation to yield prediction.

TABLE 2

| Metabolite | Correlation with yield |
|---|---|
| glutamine | 0.8874 |
| 5-oxoproline | 0.844 |
| X-14625 (glucoside of glutamine) | 0.8335 |
| aspartate | 0.824 |
| arginine | 0.8181 |
| proline | 0.8061 |
| phosphate | 0.7425 |
| homoserine-lactone | 0.7381 |
| leucine | 0.7002 |
| asparagines | 0.6725 |

The following table shows the metabolites that are negatively correlated to yield.

TABLE 3

| Metabolite | Correlation with yield |
|---|---|
| X-12792 | −0.8659 |
| N6-acetyllysine | −0.8433 |
| succinate | −0.8179 |
| N-acetylproline | −0.799 |
| 3-methoxytyrosine | −0.796 |
| X-14738 | −0.7919 |
| s-adenosylmethionine (SAM) | −0.7819 |
| X-11713 | −0.7623 |
| X-13878 | −0.7429 |
| myo-inositol | −0.73 |

The following table measures the rate of change for each identified metabolite. The rate of change is a factor in determining correlation with grain yield.

The following table identifies the metabolites highly correlated with yield. The increase of amino acids observed in this study primarily resided in the main nitrogen entry points of glutamate and aspartate family of amino acids.

TABLE 5

| Metabolite | Type | Function |
|---|---|---|
| glutamine | Amino acid | Glutamate metabolism |
| aspartate | Amino acid | Alanine and aspartate metabolism |
| proline | Amino acid | Urea cycle; arginine-, proline-, metabolism |
| 5-oxoproline | Amino acid | Glutathione metabolism |
| X - 14625 (glucoside of glutamate) | Amino acid | Glutamate metabolism |
| arginine | Amino acid | Urea cycle; arginine-, proline-, metabolism |
| phosphate | Energy | Oxidative phosphorylation |
| leucine | Amino acid | Valine, leucine and isoleucine metabolism |
| homoserine lactone | Amino acid | Glycine, serine and threonine metabolism |
| asparagine | Amino acid | Alanine and aspartate metabolism |

Example 3

Re-Analysis of Metabolic Data

Data Normalization and Preprocessing:

Raw and imputed data generated in Example 2 was reanalyzed using different methods. The raw data consisted of measurements of all of the metabolites identified in the study by various chromatographic methods. The imputed data is the raw data that has been median normalized where missing values are imputed using the lowest value of a given metabolite. Either raw or imputed data was loaded into SimcaP+12™ software from Umetrics™. All of the metabolite values for the various samples were entered as "X" variables and yield and NUE data were designated "Y" variables. There were a

TABLE 4

| | Fold of Change | | | | | | | | | | | | | | | |
|---|---|---|---|---|---|---|---|---|---|---|---|---|---|---|---|---|
| | 700 | | | | 701 | | | | 702 | | | | 703 | | | |
| BIOCHEMCIAL NAME | 2/1 | 3/1 | 4/1 | 5/1 | 2/1 | 3/1 | 4/1 | 5/1 | 2/1 | 3/1 | 4/1 | 5/1 | 2/1 | 3/1 | 4/1 | 5/1 |
| 5-oxoproline | 1.85 | 1.60 | 1.53 | 1.75 | 1.35 | 2.18 | 2.39 | 2.02 | 1.66 | 1.81 | 1.79 | 2.20 | 1.14 | 1.78 | 1.93 | 1.62 |
| alanine | 1.42 | 0.95 | 0.83 | 1.03 | 1.24 | 1.29 | 1.58 | 1.21 | 1.06 | 0.99 | 1.10 | 1.30 | 1.06 | 1.30 | 1.34 | 1.29 |
| arginine | 2.57 | 2.00 | 1.84 | 2.91 | 1.30 | 2.08 | 2.55 | 2.62 | 1.16 | 1.66 | 1.85 | 2.12 | 1.02 | 1.93 | 2.25 | 2.21 |
| asparagine | 2.62 | 1.87 | 1.86 | 3.30 | 1.59 | 3.99 | 6.67 | 7.25 | 1.17 | 1.63 | 1.92 | 2.30 | 1.00 | 2.00 | 2.03 | 2.11 |
| aspartate | 1.31 | 2.04 | 1.92 | 1.96 | 1.51 | 2.00 | 1.79 | 1.73 | 1.46 | 2.04 | 2.09 | 1.80 | 0.94 | 1.42 | 1.59 | 1.56 |
| cysteine | 0.94 | 0.55 | 0.85 | 0.71 | 0.71 | 0.93 | 0.85 | 0.65 | 1.69 | 1.18 | 0.99 | 1.67 | 1.21 | 1.05 | 1.05 | 1.09 |
| glutamate | 1.06 | 1.19 | 1.25 | 0.97 | 0.87 | 1.08 | 0.88 | 0.85 | 1.29 | 2.24 | 1.79 | 1.23 | 0.72 | 0.79 | 0.98 | 0.89 |
| glutamine | 1.84 | 1.84 | 1.71 | 1.81 | 1.58 | 2.42 | 2.55 | 2.51 | 1.42 | 1.78 | 1.73 | 1.87 | 1.24 | 1.81 | 1.80 | 1.71 |
| glycine | 1.40 | 0.87 | 0.85 | 1.07 | 1.09 | 1.41 | 1.79 | 1.38 | 1.07 | 1.21 | 1.29 | 1.39 | 0.79 | 1.01 | 1.02 | 1.19 |
| histidine | 2.74 | 1.87 | 1.37 | 1.60 | 2.47 | 2.35 | 2.34 | 1.49 | 1.64 | 1.70 | 1.68 | 1.45 | 1.27 | 1.42 | 1.69 | 1.23 |
| isoleucine | 2.35 | 1.70 | 1.30 | 1.18 | 2.07 | 1.35 | 1.14 | 0.71 | 1.58 | 1.59 | 1.25 | 1.40 | 1.29 | 1.01 | 1.12 | 0.86 |
| leucine | 1.88 | 1.61 | 1.45 | 1.60 | 1.54 | 1.64 | 1.80 | 1.42 | 1.36 | 1.63 | 1.38 | 1.64 | 1.23 | 1.25 | 1.41 | 1.33 |
| lysine | 1.59 | 1.38 | 1.22 | 1.56 | 1.16 | 1.46 | 1.58 | 1.37 | 1.38 | 1.24 | 1.14 | 1.47 | 0.89 | 0.93 | 1.37 | 0.89 |
| methionine | 1.33 | 1.34 | 1.19 | 1.10 | 1.15 | 1.13 | 1.25 | 0.85 | 0.88 | 1.08 | 0.91 | 1.16 | 1.11 | 0.86 | 0.99 | 0.95 |
| phenylalanine | 1.23 | 1.26 | 1.16 | 1.15 | 1.15 | 1.07 | 1.18 | 0.83 | 0.95 | 1.16 | 1.00 | 1.16 | 1.12 | 0.98 | 1.07 | 1.05 |
| proline | 3.01 | 2.84 | 2.19 | 2.95 | 1.84 | 3.10 | 3.15 | 4.50 | 1.71 | 3.10 | 3.46 | 3.45 | 1.30 | 2.54 | 2.62 | 3.18 |
| serine | 1.36 | 1.28 | 1.09 | 1.24 | 1.33 | 1.45 | 1.35 | 1.08 | 1.09 | 1.30 | 1.34 | 1.28 | 1.02 | 1.20 | 1.24 | 1.13 |
| threonine | 1.66 | 1.76 | 1.50 | 1.21 | 1.34 | 1.11 | 0.96 | 0.65 | 1.33 | 1.38 | 1.09 | 1.14 | 1.20 | 1.00 | 1.05 | 0.80 |
| tryptophan | 3.47 | 1.66 | 0.93 | 0.69 | 2.62 | 1.19 | 0.80 | 0.57 | 2.07 | 1.31 | 0.61 | 0.70 | 1.49 | 0.76 | 0.84 | 0.63 |
| tyrosine | 1.42 | 1.15 | 1.04 | 1.06 | 1.28 | 1.20 | 1.14 | 0.96 | 0.90 | 1.08 | 0.96 | 1.03 | 1.05 | 0.82 | 0.86 | 0.76 |
| valine | 2.18 | 1.69 | 1.35 | 1.48 | 1.51 | 1.66 | 1.75 | 1.36 | 1.26 | 1.49 | 1.41 | 1.47 | 1.26 | 1.29 | 1.39 | 1.20 | total of 1861 (8.5%) missing values in the raw data for this study. There were no missing data points with the imputed data.

Data Analysis

Principal component analysis was performed on the raw, non-imputed data to determine the greatest sources of variance. A total of 10 significant components were detected in the data. A plot of the first and second PCs indicated that there was some separation of the samples grown in low (zero additional N) compared to the other samples. That is, there were obvious changes in metabolite abundance in plants grown in lower N compared to higher N.

To determine the co-variance of metabolite abundance in relation to yield, the algorithm OPLS (orthogonal projections to latent structures) (Johan Trygg and Svante Wold, (2002) *J. Chemometrics* 16:119-128; Johan Trygg, (2002) *J. Chemometrics* 16:283-293) was applied where metabolites were "x" variables and yield was "y" variables. OPLS is similar to PLS (also called partial least squares), however, the algorithm defines orthogonal components as systematic variance, making data interpretation easier. The algorithm defines components predictive of variance in 2 matrices X and Y, in this case metabolite abundance and yield, and defines variation in X that is orthogonal (systematic) to Y. A single significant component was obtained with the raw metabolite and yield data and 2 orthogonal components that explain variance in metabolite abundance not associated with yield. A scores plot was developed and the predictive component (X-axis) and the $2^{nd}$ orthogonal component show a clear separation of the 5 different nitrogen applications associated with increasing yield.

The resulting plot clearly indicated a gradient from left to right (the predictive component of co-variance of X and Y) of low to higher N applied to the different plots in the study. The gradient from lower to higher rates of N application also correlates well with increasing yield. A loading plot of the same components was developed. The loadings are the X variables (metabolites) that explain the variance displayed in the scores plot. In the loadings plot, the metabolites follow the same X axis, so that metabolites at the right of the axis have the lowest loadings (essentially the lowest correlation to yield) and the metabolites at the right have the highest loadings, or highest correlation to increasing yield.

These results are highly similar to the results obtained in Example 2 using more standard statistical determination of correlation. All of the ten metabolites were confirmed as being highly correlated with yield using OPLS. In addition, asparagines and putrescine were also identified as being highly correlated with yield.

In order to make a more thorough comparison to the analyses performed in Example 2, the imputed data were also analyzed using OPLS. The imputation was performed by filling in the missing values for a given metabolite with the lowest value of that metabolite across all of the samples. The data were also scaled to the median of each metabolite across all of the samples. The overall variance of the imputed data was significantly different from the raw data as indicated by principal components analysis. However, the correlation of metabolite abundance to yield using the imputed data was strikingly similar to the data obtained with the raw data. As with the raw data, OPLS identified only a single significant component predictive of metabolite abundance and higher yield. The plot generated is similar to the previous plot and shows a clear separation of samples with increasing yield values and increasing rates of N input. Thus, using either raw or imputed metabolite data, the same metabolites were identified as having higher correlation to yield, and the metabolites closely match the results obtained in Example 2 using standard statistical methods. The twelve metabolites positively correlated with yield are in the following table:

TABLE 6

| Metabolite | Type | Function |
| --- | --- | --- |
| glutamine | Amino acid | Glutamate metabolism |
| aspartate | Amino acid | Alanine and aspartate metabolism |
| proline | Amino acid | Urea cycle; arginine-, proline-, metabolism |
| 5-oxoproline | Amino acid | Glutathione metabolism |
| X - 14625 (glucoside of glutamate) | Amino acid | Glutamate metabolism |
| arginine | Amino acid | Urea cycle; arginine-, proline-, metabolism |
| phosphate | Energy | Oxidative phosphorylation |
| leucine | Amino acid | Valine, leucine and isoleucine metabolism |
| homoserine lactone | Amino acid | Glycine, serine and threonine metabolism |
| asparagine | Amino acid | Alanine and aspartate metabolism |
| putrescine | Amino acid | Polyamine metabolism |

In addition, a number of metabolites were found that were predictive of yield but had a negative correlation. The metabolites showing negative correlation are in the following table:

TABLE 7

| Metabolite | Type | Function |
| --- | --- | --- |
| 6-N-acetyllysine (6-acetamido-2-aminohexanoic acid) | Acetyl-derivation of the amino acid lysine | Epigenetics, post-translational regulation, protein metabolism |
| Succinate | Energy | Krebs cycle |
| N-acetylproline | Amino acid | Urea cycle; arginine-, proline-, metabolism |
| 3-methoxytyrosine | Derivative of the amino acid tyrosine | Protein metabolism |
| S-adenosyl-methionine (SAM) | Amino acid | Cysteine, methionine, SAM, taurine metabolism |
| Myo-inositol | Lipid | Inositol metabolism |

Four additional unknown metabolites are also negatively correlated with yield, X-12792, X-14738, X11713, and X-13878.

Example 4

Second Metabolic Profile Study

Following the general methods described in Examples 1 and 2, the global metabolic profiles in ear shoots were obtained from twenty five corn genotypes, grown under five different nitrogen regimens, zero (no added nitrogen), 56, 112, 168, 224 Kg/Hectare, were studied. Field data obtained for each of the 25 genotypes was used to find a correlation of the metabolite with yield. Consistent with the findings of Example 2, many amino acids, including nitrogen carriers asparagine and glutamine, as well as the purine metabolite allantoin, were found to show strong correlations with grain yield.

For visualization of biochemical differences between the various treatment groups, the data are displayed in line plot format. The data selected for display by line plot were filtered by statistics or included for completion of a biochemical pathway. Correlation analysis for yield was carried out using the log transformed value for each metabolite and the corresponding yield (Mg/Hectare) for individual plants. Both the entire data set and selected parts of the data set were used for this analysis. The p-value and the q-value were computed to assess the statistical significance. Greater than 125 metabolites showed a correlation with yield at a statistical significance of p=<0.05. Of these the top twenty metabolites that correlated positively with yield are shown in the table below, and twenty metabolites that correlated negatively with yield are shown in second table below.

TABLE 8

Metabolites that have a positive correlation with yield.

| Biochemical Name | p-value | q-value | CORRELATION-yield |
| --- | --- | --- | --- |
| asparagine | 0.00E+00 | 0.00E+00 | 0.5335 |
| homoserine lactone | 0.00E+00 | 0.00E+00 | 0.48 |
| proline | 0.00E+00 | 0.00E+00 | 0.4423 |
| glutamine | 0.00E+00 | 0.00E+00 | 0.437 |
| glycine | 0.00E+00 | 0.00E+00 | 0.4235 |
| arginine | 0.00E+00 | 0.00E+00 | 0.4072 |
| alanine | 0.00E+00 | 0.00E+00 | 0.3917 |
| 5-oxoproline | 0.00E+00 | 0.00E+00 | 0.3562 |
| valine | 0.00E+00 | 0.00E+00 | 0.3558 |
| serine | 0.00E+00 | 0.00E+00 | 0.3347 |
| 2-aminobutyrate | 0.00E+00 | 0.00E+00 | 0.326 |
| cyano-alanine | 0.00E+00 | 0.00E+00 | 0.3247 |
| leucine | 0.00E+00 | 0.00E+00 | 0.3045 |
| X - 14625 | 0.00E+00 | 0.00E+00 | 0.2939 |
| aspartate | 0.00E+00 | 0.00E+00 | 0.2854 |
| homoserine | 0.00E+00 | 0.00E+00 | 0.285 |
| beta-alanine | 0.00E+00 | 0.00E+00 | 0.2827 |
| allantoin | 0.00E+00 | 1.00E-06 | 0.246 |
| X - 13757 | 0.00E+00 | 1.00E-06 | 0.243 |
| ophthalmate | 0.00E+00 | 1.00E-06 | 0.2425 |

The metabolite X-14625 was confirmed to be a glucoside of glutamate. All the metabolites identified in Example 2 are also identified as positively correlated with yield, except phosphate. While any of the identified positively correlated metabolites could be used to predict yield, within the top ten metabolites with the highest correlation for both studies, glutamine, 5-oxyproline, arginine, proline, and homoserine lactone are shown to be highly correlated to yield.

TABLE 9

Top twenty metabolites that correlate negatively with yield.

| Biochemical Name | p-value | q-value | CORRELATION-yield |
| --- | --- | --- | --- |
| X - 13881 | 0.00E+00 | 0.00E+00 | -0.3517 |
| threonine | 0.00E+00 | 0.00E+00 | -0.3299 |
| X - 13878 | 0.00E+00 | 0.00E+00 | -0.3145 |
| choline phosphate | 0.00E+00 | 0.00E+00 | -0.2904 |
| Isobar: 1-kestose, levan | 0.00E+00 | 0.00E+00 | -0.2793 |
| X - 13885 | 0.00E+00 | 0.00E+00 | -0.2765 |
| N6-acetyllysine | 0.00E+00 | 0.00E+00 | -0.2731 |
| X - 15326 | 0.00E+00 | 0.00E+00 | -0.2694 |
| X - 17815 | 0.00E+00 | 0.00E+00 | -0.2681 |
| adenosine-2',3'-cyclic monophosphate | 0.00E+00 | 0.00E+00 | -0.2495 |
| cytosine-2',3'-cyclic monophosphate | 0.00E+00 | 1.00E-06 | -0.2435 |
| X - 13130 | 0.00E+00 | 1.00E-06 | -0.2386 |
| glycerol 3-phosphate (G3P) | 1.00E-06 | 5.00E-06 | -0.2263 |
| X - 14734 | 1.00E-06 | 5.00E-06 | -0.2253 |
| guanosine-2',3'-cyclic monophosphate | 1.00E-06 | 7.00E-06 | -0.2222 |
| tryptophan | 3.00E-06 | 1.30E-05 | -0.2166 |
| X - 14752 | 3.00E-06 | 1.40E-05 | -0.2156 |

TABLE 9-continued

Top twenty metabolites that correlate negatively with yield.

| Biochemical Name | p-value | q-value | CORRELATION-yield |
| --- | --- | --- | --- |
| X - 13896 | 1.10E-05 | 4.70E-05 | -0.2032 |
| X - 13046 | 1.90E-05 | 0.0001 | -0.1973 |
| 2-aminoadipate | 2.60E-05 | 0.0001 | -0.1944 |

Comparing the studies in Example 2 and Example 4, X-13878, 3-methoxytyrosine, N6-acetyllysine, and 2-aminoadipate have shown consistent negative correlation with yield.

As stated before, the results in Tables 5 and 6 are consistent with metabolites that were found to correlate with yield in Examples 1 and 2 in which 4 genotypes were tested. The main class of metabolites that correlated positively with yield were amino acids, including those involved in nitrogen storage and transport i.e. glutamine and asparagine. Small differences in the correlation coefficient between the two studies can be accounted for by a slight difference in methodology and power of the studies. In Example 2, the correlation analysis was carried out with the group mean of each metabolite, and for yield, for a particular genotype. In this Example, analysis was done on data obtained for individual samples, resulting in a higher variability. Genetic diversity of the material tested may also have contributed to the variability, as the correlations in this study were calculated with data from 25 genotypes verses 4 genotypes.

Example 5

Multivariate Modeling of Yield

Using the metabolomic data collected for Example 4 on the 25 maize genotypes grown under varying nitrogen conditions, a forward selection statistical approach was used to determine the optimum number of compounds to use to give the best prediction of yield. Forward selection starts by finding the compound which is most highly correlated with either the yield response, then searches for the next best compound which improves the prediction, and so on. It is important to note that all compounds which are highly correlated to the yield do not necessarily need to be included in the model, in that their predictive power may already be accounted for. The forward selection process is reiterated until the predictive power reaches a plateau, as determined by a cross-validation procedure. This process does not choose compounds, but only the optimum number, based on averages, that will give the best predictive power.

Once the optimum number of compounds is determined, model fitting is performed to determine a group of compounds giving good predictive power. Many models are possible, and the models shown here are only examples. The statistical program JMP® (SAS, Inc.) was used for model fitting.

The maximum predictability for yield occurs when 3 metabolites are used in combination. The three metabolites are glutamine, valine and vanillate. As can be seen in the Examples above, glutamine has a very strong correlation with yield. Valine and vanillate were not identified in the top metabolites associated with yield, as they fell into the lower 50% range. However, in the model, the different mode of action of prediction power enables valine and vanillate to augment the already strong predictive power of glutamine.

In addition, maximum predictability for yield occurs when eleven metabolites are used in combination. The eleven metabolites are homoserine lactone, threonine, adenine, aminopentanate, erythritol, nicotinate ribonucleoside, arginine, 1,3-dihydroxyacetone, lysine and methyl-2-oxopentanoate.

Although the foregoing invention has been described in some detail by way of illustration and example for purposes of clarity and understanding, it will be clear to those of skill in the art that certain changes and modifications may be practiced within the scope of the appended claims.

The invention claimed is:

1. A method of forecasting crop yields, the method comprising;
   a) sampling un-pollinated female inflorescence tissue from a subset of plants of a plant population;
   b) measuring one or more yield metabolite markers for each tissue sampled from the subset plant population of a), wherein the yield metabolite markers are selected from the group consisting of glutamine, glucoside of glutamate, 5-oxoproline, aspartate, arginine, proline, phosphate, homoserine-lactone, leucine, asparagines, putrescine, valine, vanillate, threonine, adenine, aminpentanoate, erythritol, nicotinate ribonucleoside, arginine, 1,3-dihydroxyacetone, isoleucylglutamate, lysine, methy-2-oxopentanoate;
   c) comparing yield metabolite marker levels measured in b) against a calibration curve wherein the calibration curve correlates grain yield with yield metabolite marker levels measured in un-pollinated female inflorescence tissue; and
   d) forecasting crop yields.

2. The method of claim 1, wherein grain yield is predicted in a unit per area calculation.

3. The method of claim 1, wherein the plant population consists of monocots.

4. The method of claim 3, wherein the plant population comprise members of the Poaceae family.

5. The method of claim 4, wherein the plant population comprises plants selected from the group consisting of maize, rice and wheat.

6. The method of claim 1, wherein the un-pollinated female inflorescence tissue consist of any one of the following: spikelet tissue, bract tissue, spikelet meristem tissue, inflorescence stalk tissue, and immature floral tissue.

7. The method of claim 6, wherein the plant is maize and the un-pollinated female inflorescence tissue is immature floral tissue.

8. The method of claim 7, wherein the immature floral tissue is immature ear shoots.

9. The method of claim 1, wherein the yield metabolite marker levels are measured using any one of the following methods HPLC, spectrophotometry, enzymatic determination or chemical analysis.

10. The method of claim 1, wherein the method predicts the total grain yield of a plant population in one growing season.

11. The method of claim 1, wherein the calibration curve correlates units per area of a grain to units per volume of one or more yield metabolite markers.

12. The method of claim 1, wherein the yield metabolite markers are selected from the group consisting of any one or a combination of glutamine, 5-oxoproline, glucoside of glutamate, aspartate, arginine, proline, phosphate, homoserine-lactone, leucine, asparagines and putrescine.

13. The method of claim 12, wherein the yield metabolite marker is glutamine.

14. The method of claim 1, wherein the yield metabolite markers are glutamine, valine and vanillate.

15. The method of claim 1, wherein the yield metabolite markers are homoserine lactone, threonine, adenine, aminpentanoate, erythritol, nicotinate ribonucleoside, arginine, 1,3-dihydroxyacetone, isoleucylglutamate, lysine and methy-2-oxopentanoate.

16. The method of claim 1, wherein the measurements of b) are averaged and compared to the calibration curve of c).

* * * * *